US007763450B2

(12) United States Patent
Robinson et al.

(10) Patent No.: US 7,763,450 B2
(45) Date of Patent: Jul. 27, 2010

(54) FUNCTIONAL INFLUENZA VIRUS-LIKE PARTICLES (VLPS)

(75) Inventors: Robin A. Robinson, Dickerson, MD (US); Peter M. Pushko, Frederick, MD (US)

(73) Assignee: Novavax, Inc., Rockville, MD (US)

( * ) Notice: Subject to any disclaimer, the term of this patent is extended or adjusted under 35 U.S.C. 154(b) by 618 days.

(21) Appl. No.: 11/372,466

(22) Filed: Mar. 10, 2006

(65) Prior Publication Data

US 2006/0263804 A1 Nov. 23, 2006

Related U.S. Application Data

(63) Continuation of application No. 10/617,569, filed on Jul. 11, 2003.

(51) Int. Cl.
*C12N 7/00* (2006.01)
*C12N 7/04* (2006.01)
(52) U.S. Cl. .................... 435/235.1; 435/69.1; 435/236
(58) Field of Classification Search .................. 435/236
See application file for complete search history.

(56) References Cited

U.S. PATENT DOCUMENTS

| 6,649,372 | B1 | 11/2003 | Palese et al. |
| 2003/0035814 | A1 | 2/2003 | Kawaoka et al. |
| 2005/0009008 | A1 | 1/2005 | Robinson et al. |

FOREIGN PATENT DOCUMENTS

| WO | WO 96/37624 | 11/1996 |
| WO | WO 02/00085 A2 | 1/2002 |
| WO | WO 02/00885 A2 | 1/2002 |

OTHER PUBLICATIONS

Saito, T., et al., "Characterization of a human H9N2 influenza virus isolated in Hong Kong," *Vaccine* 20(1-2):125-133 (2001).
Gupta, R.K., et al., "Adjuvant properties of non-phospholipid liposomes (Novasomes) in experimental animals for human vaccine antigens," *Vaccine* 14(3):219-225 (1996).
Ali, Ayub et al., "Influenza Virus Assembly: Effect of Influenza Virus Glycoproteins on the Membrane Association of M1 Protein", *Journal of Virology*, Sep. 2000, vol. 74, No. 18, pp. 8709-8719.
Bullido, Rosario et al., "Several Protein Regions Contribute to Determine the Nuclear and Cytoplasmic Localization of the Influenza A Virus Nucleoprotein", *Journal of General Virology*, 2000, 81, pp. 135-142.
Castrucci, Maria R. et al., "Reverse Genetics System for Generation of an Influenza A Virus Mutant Containing a Deletion of the Carboxyl-Terminal Residue of M2 Protein", *Journal of Virology*, May 1995, vol. 69, No. 5, pp. 2725-2728.
Elster, Christine et al., "Influenza Virus M1 Protein Binds to RNA Through Its Nuclear Localization Signal", *Journal of General Virology*, 1997, 78, pp. 1589-1956.

Fodor, Ervin et al., "Rescue of Influenza A Virus from Recombinant DNA", *Journal of Virology*, Nov. 1999, vol. 73, No. 11, pp. 9679-9682.
Gómez-Puertas, Paulino et al., "Efficient Formation of Influenza Virus-Like Particles: Dependence on the Expression Levels of Viral Proteins", *Journal of General Virology*, 1999, 80 pp. 1635-1645.
Gómez-Puertas, Paulino et al., "Influenza Virus Matrix Protein is the Major Driving Force in Virus Budding", *Journal of Virology*, Dec. 2000, vol. 74, No. 24, pp. 11538-11547.
Hoffmann, Erich et al., "A DNA Transfection System for Generation of Influenza A Virus from Eight Plasmids", *PNAS*, May 23, 2000, vol. 97, No. 11, pp. 6108-6113.
Kuroda, Kazumichi et al., "Expression of the Influenza virus Haemagglutinin in Insect Cells by a Baculovirus Vector", *The EMBO Journal*, 1986, vol. 5 No. 6, pp. 1359-1365.
Li, Shengqiang et al., "Chimeric Influenza Virus Induces Neutralizing Antibodies and Cytotoxic T Cells Against Human Immunodeficiency Virus Type 1", *Journal of Virology*, Nov. 1993, vol. 67, No. 11, pp. 6659-6666.
Lyles, Douglas S. et al. "Subunit Interactions of Vesicular Stomatitis Virus Envelope Glycoprotein Stablilized by Binding to Viral Matrix Protein", *Journal of Virology*, Jan. 1992, vol. 66 No. 1, pp. 349-358.
Mena, Ignacio et al., "Rescue of a Synthetic Chloramphenicol Acetyltransferase RNA into Influenza Virus-Like Particles Obtained from Recombinant Plasmids", *Journal of Virology*. Aug. 1996, vol. 70, No. 8, pp. 5016-5024.
Neumann, Gabriele et al., "Generation of Influenza A Viruses Entirely from Cloned cDNAs", *Proc. Natl. Acad. Sci USA*, Aug. 1999, vol. 96, pp. 935-9350.
Pattnaik, Asit K. et al., "Formation of Influenza Virus particles Lacking Hemagglutinin on the Viral Envelope", *Journal of Virology*, Dec. 1986, vol. 60, No. 3, pp. 994-1001.
Pleschka, Stephan et al., "A Plasmid-Based Reverse Genetics System for Influenza A Virus", *Journal of Virology*, Jun. 1996, vol. 70, No. 6, pp. 4188-4192.

(Continued)

*Primary Examiner*—Mary E Mosher
*Assistant Examiner*—Myron G Hill
(74) *Attorney, Agent, or Firm*—Cooley LLP

(57) ABSTRACT

Recombinant influenza virus proteins, including influenza capsomers, subviral particles, virus-like particles (VLP), VLP complexes, and/or any portions of thereof, are provided as a vaccine for influenza viruses. The invention is based on the combination of two vaccine technologies: (1) intrinsically safe recombinant vaccine technology, and (2) highly immunogenic, self-assembled protein macromolecules embedded in plasma membranes and comprised of multiple copies of influenza virus structural proteins exhibiting neutralizing epitopes in native conformations. More specifically, this invention relates to the design and production of functional homotypic and heterotypic recombinant influenza virus-like particles (VLPs) comprised of recombinant structural proteins of human influenza virus type A/Sydney/5/94 (H3N2) and/or avian influenza virus type A/Hong Kong/1073/99 (H9N2) in baculovirus-infected insect cells and their application as a vaccine in the prevention of influenza infections and as a laboratory reagent for virus structural studies and clinical diagnostics.

18 Claims, 12 Drawing Sheets

OTHER PUBLICATIONS

Figure 5:
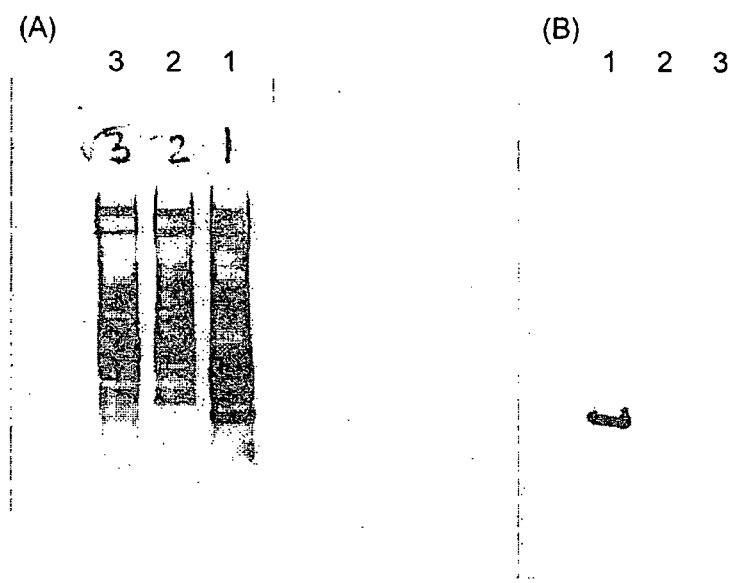

St. Angelo, Carol et al., "Two of the Three Influenza Viral Polymerase Proteins Expressed by Using Baculovirus Vectors Form a Complex in Insect Cells", *Journal of Virology*, Feb. 1987, vol. 61, No. 2, pp. 361-365.

Tobita, Kiyotake et al., "Spontaneous Excretion of Virus from MDCK Cells Persistently Infected with Influenza Virus A/PR/8/34", *Journal of General Virology*, 1997, 78, pp. 563-566.

Yasuda, Jim et al., "Growth Control of Influenza A Virus by MI Protein: Analysis of Transfectant Viruses Carrying the Chimeric M Gene", *Journal of Virology*, Dec. 1994, vol. 68, No. 12, pp. 8141-8146.

Ye, Zhiping et al., "Nucleus-Targeting Domain of the Matrix Protein (MI) of Influenza Virus", *Journal of Virology*, Mar. 1995, vol. 69, No. 3, pp. 1964-1970.

Zhao, Hongxing et al., "The MI and NP Proteins of Influenza A Virus Form Homo- but not Heterooligomeric Complexes when Coexpressed in BHK-21 Cells", *Journal of General Virology*, 1998, 79, pp. 2435-2446.

Crowther, R.A., et al., "Three-Dimensional Structure of Hepatitis B. Virus Core Particles Determined by Electron Cryomicroscopy," *Cell*, vol. 77, pp. 943-950, Jun. 17, 1994.

Murphy, Brian R. and Robert G. Webster, *Orthomyxoviruses, Fields Virology, Third Edition*, vol. 1, pp. 1397-1445, 1996.

Zhou, Xianzehng et al., "Generation of Cytotoxic and Humoral Immune-Responses by Non-replicative Recombinant Semlike Forest Virus," *Proc. Natl. Acad. Sci. USA*, vol. 92, pp. 3009-3013, Mar. 1995.

Treanor, John J. et al., "Evaluation of a Recombinant Hemagglutinin Expressed in Insect Cells as an Influenza Vaccine in Young an Elderly Adults," *The Journal of Infectious Diseases*, vol. 173, pp. 1467-1470, 1996.

Lakey, et al., "Recombinant Baculovirus Influenza A Hemagglutinin Vaccines are Well Tolerated and Immunogenic in Healthy Adults, Concise Communications" *JID* 1996; 174 (October) pp. 838.841.

Johansson, Bert E., "Immunization with Influenza A Virus Hemagglutinin and Neuraminidase Produced in Recobinant Baculovirus Results in a Balanced and Broadened Immune Response Superior to Conventional Vaccine," *Vaccine* 17, pp. 2073-2080 (1999).

Pushko, Peter et al., "Replicon-Helper Systems from Attenuated Venezuelan Equine Encephalitis Virus: Expression of Heterologous Genes in Vitro and Immunization Against Heterologous Pathogens in Vivo," *Virology*, vol. 239, pp. 389-401 (1997).

Ulmer, Jeffrey B. et al., "Heterologous Protection Against Influenza by Injection of DNA Encoding a Viral Protein," *Science*, vol. 259, Mar. 19, 1993, pp. 1745-1749.

Berglund, Peter et al., "Immunization with Recombinant Semlike Forest Virus Induces Protection Against Influenza Challenge in Mice," *Vaccine* 17 (1999) pp. 497-507.

Cox, John C. and Ann R. Coulter, "Adjuvants—A Classification and Review of Their Modes of Action," *Vaccine*, vol. 15, No. 3, pp. 248-256, 1997.

Crawford, John et al., "Baculovirus-Derived Hemagglutinin Vaccines Protect Against Lethal Influenza Infections by Avian H5 and H7 Subtypes," *Vaccine* 17 (1999), pp. 2265-2274.

Latham, Theresa and Jose M. Galarza, "Formation of Wild-Type and Chimeric Influenza Virus-Like Particles Following Simultaneous Expression of Only Four Structural Proteins," *Journal of Virology*, Jul. 2001, vol. 75, pp. 6154-6165.

Tsuji, et al, "Recombinant Sindbis Viruses Expressing a Cytotoxic T-Lymphocyte Epitope of a Malaria Parasite or of Influenza Virus Elicit Protection Against the Corresponding Pathogen in Mice," *Journal of Virology*, Aug. 1998, pp. 6907-6910.

Neumann, Gabriele et al., "Plasmid-Driven Formation of Influenza Virus-Like Particles," *Journal of Virology*, Jan. 2000, pp. 547-551.

Peiris, J.S.M. et al., "Co-circulation of Avian H-N2 and Contemporary "Human" H3N2 Influenza A Viruses in Pigs in Southeastern China: Potential for Genetic Reassortment?" *Journal of Virology*, Oct. 2001, pp. 9679-9686.

Ulmer, Jeffrey B. et al., "Protective D4+ and CD8+ T Cells against Influenza Virus Induced by Vaccination with Nucleoprotein DNA," *Journal of Virology*, Jul. 1998, pp. 5648-5653.

Watanabe, Tokiko et al., "Immunogenicity and Protective Efficacy of Replication-Incompetent Influenza Virus-Like Particles," *Journal of Virology*, Jan. 2002, pp. 767-773.

Olsen, Christopher W. et al., "Immunogenicity and Efficacy of Baculovirus-Expressed and DNA-Based Equine Influenza Virus Hemagglutinin Vaccines in Mice," *Vaccine*, vol. 15, No. 10., pp. 1149-1156, 1997.

Slepushkin, Vladimir A. et al., "Protection of Mice Against Influenza A Virus Challenge by Vaccination With Baculovirus-Expressed M2 Protein," *Vaccine*, vol. 13, No. 15, pp. 1399-1402, 1995.

Pumpens, Paul and Elmars Grens, "Artificial Genes for Chimeric Virus-Like Particles," *Artificial DNA* (Khudyakov, Y.E., and Fields, H.A., Eds.) pp. 249-327. CRC Press, New York (2003).

Saito, et al., "Characterization of a human H9N2 influenza virus isolated in Hong Kong," *Vaccine* 20(1-2): 125-133 (Oct. 12, 2001), Butterworth Scientific, Guildford, Great Britain.

Matassov, et al., "A novel intranasal virus-like particle (VLP) vaccine designed to protect against the pandemic 1918 influenza A virus (H1N1)," *Viral Immunology* 20(3): 441-452 (Sep. 2007), Mary Ann Liebert, Inc., United States.

Crowther, et al., Three-dimensional structure of hepatitis B virus core particles determined by electron cryomicroscopy, *Cell* 77: 943-950 (Jun. 17, 1994), Cell Press, United States.

Murphy, et al., "Orthomyxoviruses," *Fields Virology*, Third Edition, vol. 1: 1397-1445, 1996.

Zhou, et al., "Generation of cytotoxic and humoral immune responses by non-replicative recombinant semlike forest virus," *Proc. Natl. Acad. Sci. USA* 92: 3009-3013 (Mar. 1995).

Treanor, et al., "Evaluation of a recombinant hemagluttinin expressed in insect cells as an influenza vaccine in young and elderly adults," *The Journal of Infectious Diseases* 173: 1467-1470 (1996).

Lakey, et al., "Recombinant baculovirus influenza A hemagluttinin vaccines are well tolerated and immunogenic in healthy adults," *Concise Communications JID* 174: 838-841 (Oct. 1996).

Johansson, et al., "Immunization with influenza A virus hemagglutinin and neuraminidase produced in recombinant baculovirus results in a balanced and broadened immune response superior to conventional vaccine," *Vaccine* 17: 2073-2080 (1999), Butterworth Scientific, Guildford, Great Britain.

Pushko, et al., Replicon-helper systems from attenuated Venezuelan equine encephalitis virus: expression of heterologous genes in vitro and immunization against heterologous pathogens in vivo, *Virology* 239: 389-401 (1997).

Ulmer, et al., "Heterologous protection against influenza by injection of DNA encoding a viral protein," *Science* 259: 1745-1749 (Mar. 19, 1993).

Cox, et al., "Adjuvants—A classification and review of their modes of action," *Vaccine* 15(3): 248-256 (1997), Butterworth Scientific, Guildford, Great Britain.

Tsuji, et al., "Recombinant sindbis viruses expressing a cytotoxic T-lymphocyte epitope of a malaria parasite or of influenza virus elicit protection against the corresponding pathogen in mice," *J. of Virology* 72(8): 6907-6910 (Aug. 1998), American Society for Microbiology, United States.

Peiras, et al., "Co-circulation of avian H-N2 and contemporary "human" H3N2 influenza A viruses in pigs in southeastern China: Potential for genetic reassortment?" *J. of Virology*, 75(20); 9679-9686, (Oct. 2001), American Society for Microbiology, United States.

Ulmer, et al., "Protective D4+ and CD8+ T cells against influenza virus induced by vaccination with nucleoprotein DNA," *J. of Virology* 72(7): 5648-5653 (Jul. 1998), American Society for Microbiology, United States.

Olsen, et al., "Immunogenicity and efficacy of baculovirus-expressed and DNA-based equine influenza virus hemagluttinin vaccines in mice," *Vaccine* 15(10): 1149-1156 (1997), Butterworth Scientific, Guildford, Great Britain.

Slepushkin, et al., "Protection of mice against influenza A virus challenge by vaccination with baculovirus-expressed M2 protein," *Vaccine* 13(15): 1399-1402 (1995), Butterworth Scientific, Guildford, Great Britain.

Pumpens, et al., "Artificial genes for chimeric virus-like particles," *Artificial DNA* (Khudyakov, Y.E. and Fields, H.A., Eds.), pp. 249-327, CRC Press, New York (2003).

Ali et al., "Influenza virus assembly: effect of influenza virus glycoproteins on the membrane association of M1 protein," *J. of Virology* 74(18): 8709-8719 (Sep. 2000), American Society for Microbiology, United States.

Bullido, et al., "Several protein regions contribute to determine the nuclear and cytoplasmic localization of the influenza A virus nucleoprotein," *J. of General Virology* 81: 135-142 (2000).

Castrucci, et al., "Reverse genetics system for generation of an influenza A virus mutant containing a deletion of the carboxyl-terminal residue of M2 protein," *J. of Virology* 69(5): 2725-2728 (May 1995), American Society for Microbiology, United States.

Elster, et al., "Influenza virus M1 protein binds to RNA through its nuclear localization signal," *J. of General Virology* 78: 1589-1596 (1997).

Fodor, et al., Rescue of influenza A virus from recombinant DNA, *J. of Virology* 73(11): 9679-9682 (Nov. 1999), American Society for Microbiology, United States.

Gomez-Puertas, et al., "Efficient formation of influenza virus-like particles: dependence on the expression levels of viral proteins," *J. of General Virology* 80: 1635-1645 (1999).

Hoffmann, et al., "A DNA transfection system for generation of influenza A virus from eight plasmids," *Proc. Natl. Acad. Sci. USA* 97(11): 6108-6113 (May 23, 2000).

Kuroda, et al., "Expression of the influenza virus hemagluttinin in insect cells by a baculovirus vector," *The EMBO Journal* 5(6): 1359-1365 (1986).

Li, et al., "Chimeric influenza virus induces neutralizing antibodies and cytotoxic T cells against human immunodeficiency virus type 1," *J. of Virology* 67(11): 6659-6666 (Nov. 1993), American Society for Microbiology, United States.

Lyles, et al., "Subunit interactions of vesicular stomatitis virus envelope glycoprotein stabilized by binding to viral matrix protein," *J. of Virology* 66(1): 349-358 (Jan. 1992), American Society for Microbiology, United States.

Mena, et al., "Rescue of a synthetic chloramphenicol acetyltransferase RNA into influenza virus-like particles obtained from recombinant plasmids," *J. of Virology* 70(8): 5016-5024 (Aug. 1996), American Society for Microbiology, United States.

Neumann, et al., "Generation of influenza A viruses entirely from cloned cDNAs," *Proc. Natl. Acad. Sci. USA* 96: 935-950 (Aug. 1999).

Pattnaik, et al., "Formation of influenza virus particles lacking hemagglutinin on the viral envelope," *J. of Virology* 60(3): 994-1001, (Dec. 1986), American Society for Microbiology, United States.

Pleschka, et al., "A plasmid-based reverse genetics system for influenza A virus," *J. of Virology* 70(6): 4188-4192 (Jun. 1996), American Society for Microbiology, United States.

St. Angelo, et al., "Two of the three influenza viral polymerase proteins expressed by using baculovirus vectors form a complex in insect cells," *J. of Virology* 61(2): 361-365 (Feb. 1987), American Society for Microbiology, United States.

Tobita, et al., "Spontaneous excretion of virus from MDCK cells persistently infected with influenza virus A/PR/8/34," *J. of General Virology* 78: 563-566 (1997).

Yasuda, et al., "Growth control of influenza A virus by M1 protein: analysis of transfectant viruses carrying the chimeric M gene," *J. of Virology* 68(12): 8141-8146 (Dec. 1994), American Society for Microbiology, United States.

Ye, et al., "Nucleus-targeting domain of the matrix protein (M1) of influenza virus," *J. of Virology* 69(3): 1964-1970 (Mar. 1995).

Zhao, et al., "The M1 and NP proteins of influenza A virus form homo- but not heterooligomeric complexes when coexpressed in BHK-21 cells," *J. of General Virology* 79: 2435-2446 (1998).

Avalos, Roy, et al., "Association of Influenza Virus NP and M1 Proteins with Cellular Cytoskeletal Elements in Influenza Virus-Infected Cells," *Journal of Virology*, Apr. 1997, vol. 71, pp. 2947-2958.

Bucher, et al., "M Protein (M1) of Influenza Virus: Antigenic Analysis and Intracellular Localization with Monoclonal Antibodies," *Journal of Virology*, Sep. 1989, vol. 63, pp. 3622-3633.

Chen, et al., "Comparison of the ability of viral protein-expressing plasmid DNAs to protect against influenza," Vaccine, 1998, vol. 16, 1544-1549.

Chen, et al., "Enhanced protection against a lethal influenza virus challenge by immunization with both hemagglutinin- and neuraminidase- expressing DNAs," Vaccine, 1999, vol. 17, 653-659.

Enami, et al., "Influenza Virus Hemagglutinin and Neuraminidase Glycoproteins Stimulate the Membrane Association of the Matrix Protein," *Journal of Virology*, Oct. 1996, vol. 70, pp. 6653-6657.

Huylebroeck, et al., "High-level transient expression of influenza virus proteins from a series of SV40 late and early replacement vectors," *Gene*, 1988, vol. 66, pp. 163-181.

Kretzschmar, et al., "Membrane Association of Influenza Virus Matrix Protein Does Not Require Specific Hydrophobic Domains or the Viral Glycoproteins," *Virology*, 1996, vol. 220, pp. 37-45.

Zhang, et al., "Characterization of the Membrane Association of the Influenza Virus Matrix Protein in Living Cells," *Virology*, vol. 225, pp. 225-266.

Gupta, et al., "Adjuvant properties of non-phospholipid liposomes (Novasomes®) in experimental animals for human vaccine antigens," *Vaccine* 14(3): 219-225 (Feb. 1996).

Watanabe Tokiko, et al., "Immunogenicity and protective efficacy of replication-incompetent influenza-virus like particles," *J. of Virology* 76(2): 767-773 (Jan. 2002), American Society for Microbiology, United States.

Neumann, et al., "Plasmid-driven formation of influenza virus-like particles," *J. of Virology* 74(1): 547-551 (Jan. 2000), American Society for Microbiology, United States.

Gomez-Puertas, et al., "Influenza virus matrix protein is the major driving force in virus budding," *J. of Virology* 74(24): 11538-11547 (Dec. 2000), American Society for Microbiology, United States.

Crawford, et al., "Baculovirus-derived hemagluttinin vaccines protect against lethal influenza infections by avian H5 and H7 subtypes," *Vaccine* 17(18): 2265-2274 (May 4, 1999), Butterworth Scientific, Guildford, Great Britain.

Latham, et al., "Formation of wild-type and chimeric influenza virus-like particles following simultaneous expression of only four structural proteins," *J. of Virology* 75(13): 6154-6165 (Jul. 2001), American Society for Microbiology, United States.

Pushko, et al., "Influenza virus-like particles comprised of the HA, NA, and M1 proteins of H9N2 influenza virus induce protective immune responses in BALB/c mice," *Vaccine* 23(50): 5751-5759 (Dec. 30, 2005), Butterworth Scientific, Guildford, Great Britain.

Supplementary European Search Report in European Application Serial No. EP04786052.3, mailed Mar. 26, 2008.

```
ATGAATCCAAATCAAAAGATAATAGCACTTGGCTCTGTTTCTATAACTATTGCGACAATATG
TTTACTCATGCAGATTGCCATCTTAGCAACGACTATGACACTACATTTCAATGAATGTACCA
ACCCATCGAACAATCAAGCAGTGCCATGTGAACCAATCATAATAGAAAGGAACATAACAGAG
ATAGTGCATTTGAATAATACTACCATAGAGAAGGAAAGTTGTCCTAAAGTAGCAGAATACAA
GAATTGGTCAAAACCGCAATGTCAAATTACAGGGTTCGCCCCTTTCTCCAAGGACAACTCAA
TTAGGCTTTCTGCAGGCGGGGATATTTGGGTGACAAGAGAACCTTATGTATCGTGCGGTCTT
GGTAAATGTTACCAATTTGCACTTGGGCAGGGAACCACTTTGAACAACAAACACTCAAATGG
CACAATACATGATAGGAGTCCCCATAGAACCCTTTTAATGAACGAGTTGGGTGTTCCATTTC
ATTTGGGAACCAAACAAGTGTGCATAGCATGGTCCAGCTCAAGCTGCCATGATGGGAAGGCA
TGGTTACATGTTTGTGTCACTGGGGATGATAGAAATGCGACTGCTAGCATCATTTATGATGG
GATGCTTACCGACAGTATTGGTTCATGGTCTAAGAACATCCTCAGAACTCAGGAGTCAGAAT
GCGTTTGCATCAATGGAACTTGTACAGTAGTAATGACTGATGGAAGTGCATCAGGAAGGGCT
GATACTAAAATACTATTCATTAGAGAAGGGAAAATTGTCCACATTGGTCCACTGTCAGGAAG
TGCTCAGCATGTGGAGGAATGCTCCTGTTACCCCGGTATCCAGAAGTTAGATGTGTTTGCA
GAGACAATTGGAAGGGCTCCAATAGACCCGTGCTATATAAATGTGGCAGATTATAGTGTT
GATTCTAGTTATGTGTGCTCAGGACTTGTTGGCGACACACCAAGAAATGACGATAGCTCCAG
CAGCAGTAACTGCAGGGATCCTAATAACGAGAGAGGGGGCCCAGGAGTGAAAGGGTGGGCCT
TTGACAATGGAAATGATGTTTGGATGGGACGAACAATCAAGAAAGATTCGCGCTCTGGTTAT
GAGACTTTCAGGGTCGTTGGTGGTTGGACTACGGCTAATTCCAAGTCACAAATAAATAGGCA
AGTCATAGTTGACAGTGATAACTGGTCTGGGTATTCTGGTATATTCTCTGTTGAAGGAAAAA
CCTGCATCAACAGGTGTTTTTATGTGGAGTTGATAAGAGGGAGACCACAGGAGACCAGAGTA
TGGTGGACTTCAAATAGCATCATTGTATTTTGTGGAACTTCAGGTACCATGGAACAGGCTC
ATGGCCCGATGGAGCGAATATCAATTTCATGTCTATATAA
```

FIGURE 1

```
ATGGAAACAATATCACTAATAACTATACTACTAGTAGTAACAGCAAGCAATGCAGATAAAAT
CTGCATCGGCCACCAGTCAACAAACTCCACAGAAACTGTGGACACGCTAACAGAAACCAATG
TTCCTGTGACACATGCCAAAGAATTGCTCCACACAGAGCATAATGGAATGCTGTGTGCAACA
AGCCTGGGACATCCCCTCATTCTAGACACATGCACTATTGAAGGACTAGTCTATGGCAACCC
TTCTTGTGACCTGCTGTTGGGAGGAAGAGAATGGTCCTACATCGTCGAAAGATCATCAGCTG
TAAATGGAACGTGTTACCCTGGGAATGTAGAAAACCTAGAGGAACTCAGGACACTTTTTAGT
TCCGCTAGTTCCTACCAAAGAATCCAAATCTTCCCAGACACAACCTGGAATGTGACTTACAC
TGGAACAAGCAGAGCATGTTCAGGTTCATTCTACAGGAGTATGAGATGGCTGACTCAAAAGA
GCGGTTTTTACCCTGTTCAAGACGCCCAATACACAAATAACAGGGGAAAGAGCATTCTTTTC
GTGTGGGGCATACATCACCCACCCACCTATACCGAGCAAACAAATTTGTACATAAGAAACGA
CACAACAACAAGCGTGACAACAGAAGATTTGAATAGGACCTTCAAACCAGTGATAGGGCCAA
GGCCCCTTGTCAATGGTCTGCAGGGAAGAATTGATTATTATTGGTCGGTACTAAAACCAGGC
CAAACATTGCGAGTACGATCCAATGGGAATCTAATTGCTCCATGGTATGGACACGTTCTTTC
AGGAGGGAGCCATGGAAGAATCCTGAAGACTGATTTAAAAGGTGGTAATTGTGTAGTGCAAT
GTCAGACTGAAAAAGGTGGCTTAAACAGTACATTGCCATTCCACAATATCAGTAAATATGCA
TTTGGAACCTGCCCCAAATATGTAAGAGTTAATAGTCTCAAACTGGCAGTCGGTCTGAGGAA
CGTGCCTGCTAGATCAAGTAGAGGACTATTTGGAGCCATAGCTGGATTCATAGAAGGAGGTT
GGCCAGGACTAGTCGCTGGCTGGTATGGTTTCCAGCATTCAAATGATCAAGGGGTTGGTATG
GCTGCAGATAGGGATTCAACTCAAAAGGCAATTGATAAAATAACATCCAAGGTGAATAATAT
AGTCGACAAGATGAACAAGCAATATGAAATAATTGATCATGAATTCAGTGAGGTTGAAACTA
GACTCAATATGATCAATAATAAGATTGATGACCAAATACAAGACGTATGGGCATATAATGCA
GAATTGCTAGTACTACTTGAAAATCAAAAACACTCGATGAGCATGATGCGAACGTGAACAA
TCTATATAACAAGGTGAAGAGGGCACTGGGCTCCAATGCTATGGAAGATGGGAAAGGCTGTT
TCGAGCTATACCATAAATGTGATGATCAGTGCATGGAAACAATTCGGAACGGGACCTATAAT
AGGAGAAAGTATAGAGAGGAATCAAGACTAGAAAGGCAGAAAATAGAGGGGGTTAAGCTGGA
ATCTGAGGGAACTTACAAAATCCTCACCATTTATTCGACTGTCGCCTCATCTCTTGTGCTTG
CAATGGGGTTTGCTGCCTTCCTGTTCTGGGCCATGTCCAATGGATCTTGCAGATGCAACATT
TGTATATAA
```

FIGURE 2

ATGAGTCTTCTAACCGAGGTCGAAACGTACGTTCTCTCTATCATCCCATCAGGCCCCCTCAA
AGCCGAGATCGCGCAGAGACTTGAGGATGTTTTTGCAGGGAAGAACACAGATCTTGAGGCTC
TCATGGAATGGCTAAAGACAAGACCAATCCTGTCACCTCTGACTAAGGGGATTTTAGGGTTT
GTGTTCACGCTCACCGTGCCCAGTGAGCGAGGACTGCAGCGTAGACGATTTGTCCAAAATGC
CCTAAATGGGAATGGAGACCCAAACAACATGGACAGGGCAGTTAAACTATACAAGAAGCTGA
AGAGGGAAATGACATTCCATGGAGCAAAGGAAGTTGCACTCAGTTACTCAACTGGTGCGCTT
GCCAGTTGCATGGGTCTCATATACAACCGGATGGGAACAGTGACCACAGAAGTGGCTCTTGG
CCTAGTATGTGCCACTTGTGAACAGATTGCTGATGCCCAACATCGGTCCCACAGGCAGATGG
CGACTACCACCAACCCACTAATCAGGCATGAGAACAGAATGGTACTAGCCAGCACTACGGCT
AAGGCCATGGAGCAGATGGCTGGATCAAGTGAGCAGGCAGCAGAAGCCATGGAAGTCGCAAG
TCAGGCTAGGCAAATGGTGCAGGCTATGAGGACAATTGGGACTCACCCTAGTTCCAGTGCAG
GTCTAAAAGATGATCTTATTGAAAATTTGCAGGCTTACCAGAAACGGATGGGAGTGCAAATG
CAGAGATTCAAGTGA

FIGURE 3

(A)
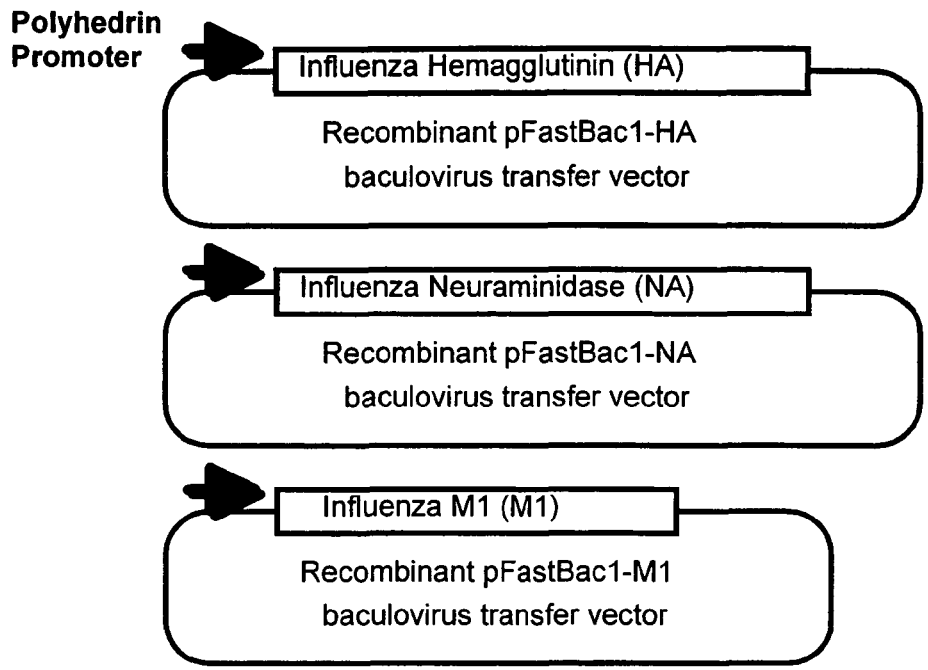
(B)
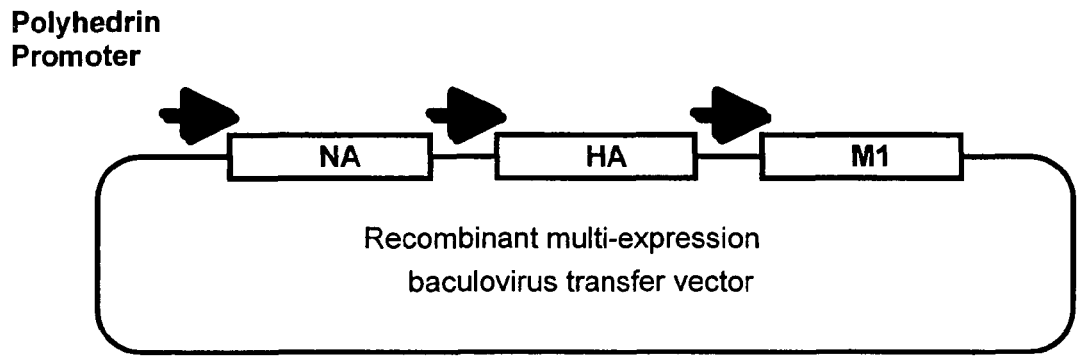
FIGURE 4

(A)  1 2 3 4 5 6 7 8 9 10 11 12 13 14 M (B)  1 2 3 4 5 6 7 8 9 10 11 12 13 14 M (C)  1 2 3 4 5 6 7 8 9 10 11 12 13 14 M

FIGURE 7

FUNCTIONAL INFLUENZA VIRUS-LIKE PARTICLES (VLPS)

This application is a continuation of U.S. patent application Ser. No. 10/617,569 filed Jul. 11, 2003 which is herein incorporated by reference in it entirety for all purposes.

BACKGROUND OF INVENTION

Influenza virus is a member of Orthomyxoviridae family (for review, see Murphy and Webster, 1996). There are three subtypes of influenza viruses designated A, B, and C. The influenza virion contains a segmented negative-sense RNA genome. The influenza virion includes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2) proteins. The HA, NA, M1, and M2 are membrane associated, whereas NP, PB1, PB2, PA, and NS2 are nucleocapsid associated proteins. The NS1 is the only nonstructural protein not associated with virion particles but specific for influenza-infected cells. The M1 protein is the most abundant protein in influenza particles. The HA and NA proteins are envelope glycoproteins, responsible for virus attachment and penetration of the viral particles into the cell, and the sources of the major immunodominant epitopes for virus neutralization and protective immunity. Both HA and NA proteins are considered the most important components for prophylactic influenza vaccines.

Influenza virus infection is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the $HA_2$ protein undergoes conformational changes that lead to fusion of viral and cell membranes and virus uncoating and M2-mediated release of M1 proteins from nucleocapsid-associated ribonucleoproteins (RNPs), which migrate into the cell nucleus for viral RNA synthesis. Antibodies to HA proteins prevent virus infection by neutralizing virus infectivity, whereas antibodies to NA proteins mediate their effect on the early steps of viral replication.

Inactivated influenza A and B virus vaccines are licensed currently for parenteral administration. These trivalent vaccines are produced in the allantoic cavity of embryonated chick eggs, purified by rate zonal centrifugation or column chromatography, inactivated with formalin or β-propiolactone, and formulated as a blend of the two strains of type A and the type B strain of influenza viruses in circulation among the human population for a given year. The available commercial influenza vaccines are whole virus (WV) or subvirion (SV; split or purified surface antigen) virus vaccines. The WV vaccine contains intact, inactivated virions. SV vaccines treated with solvents such as tri-n-butyl phosphate (Flu-Shield, Wyeth-Lederle) contain nearly all of the viral structural proteins and some of the viral envelopes. SV vaccines solubilized with Triton X-100 (Fluzone, Connaught; Fluvirin, Evans) contain aggregates of HA monomers, NA, and NP principally, although residual amounts of other viral structural proteins are present. A potential cold-adapted live attenuated influenza virus vaccine (FluMist, MedImmune) was granted marketing approval recently by the FDA for commercial usage as an intranasally delivered vaccine indicated for active immunization and the prevention of disease caused by influenza A and B viruses in healthy children and adolescents, 5-17 years of age and healthy adults 18-49 years of age.

Several recombinant products have been developed as recombinant influenza vaccine candidates. These approaches have focused on the expression, production, and purification of influenza type A HA and NA proteins, including expression of these proteins using baculovirus infected insect cells (Crawford et al, 1999; Johansson, 1999; Treanor et al., 1996), viral vectors (Pushko et al., 1997; Berglund et al, 1999), and DNA vaccine constructs (Olsen et al., 1997).

Crawford et al. (1999) demonstrated that influenza HA expressed in baculovirus infected insect cells is capable of preventing lethal influenza disease caused by avian H5 and H7 influenza subtypes. At the same time, another group demonstrated that baculovirus-expressed influenza HA and NA proteins induce immune responses in animals superior to those induced by a conventional vaccine (Johansson et al., 1999). Immunogenicity and efficacy of baculovirus-expressed hemagglutinin of equine influenza virus was compared to a homologous DNA vaccine candidate (Olsen et al., 1997). Taken together, the data demonstrated that a high degree of protection against influenza virus challenge can be induced with recombinant HA or NA proteins, using various experimental approaches and in different animal models.

Lakey et al. (1996) showed that a baculovirus-derived influenza HA vaccine was well-tolerated and immunogenic in human volunteers in a Phase I dose escalation safety study. However, results from Phase II studies conducted at several clinical sites in human volunteers vaccinated with several doses of influenza vaccines comprised of HA and/or NA proteins indicated that the recombinant subunit protein vaccines did not elicit protective immunity [G. Smith, Protein Sciences; M. Perdue, USDA, Personal Communications]. These results indicated that conformational epitopes displayed on the surface of HA and NA peplomers of infectious virions were important in the elicitation of neutralizing antibodies and protective immunity.

Regarding the inclusion of other influenza proteins in recombinant influenza vaccine candidates, a number of studies have been carried out, including the experiments involving influenza nucleoprotein, NP, alone or in combination with M1 protein (Ulmer et al., 1993; Ulmer et al., 1998; Zhou et al., 1995; Tsui et al., 1998). These vaccine candidates, which were composed of quasi-invariant inner virion proteins, elicited a broad spectrum immunity that was primarily cellular (both $CD4^+$ and $CD8^+$ memory T cells). These experiments involved the use of the DNA or viral genetic vectors. Relatively large amounts of injected DNA were needed, as results from experiments with lower doses of DNA indicated little or no protection (Chen et al., 1998). Hence, further preclinical and clinical research may be required to evaluate whether such DNA-based approaches involving influenza NP and M1 are safe, effective, and persistent.

Recently, in an attempt to develop more effective vaccines for influenza, particulate proteins were used as carriers of influenza M2 protein epitopes. The rationale for development of an M2-based vaccine was that in animal studies protective immunity against influenza was elicited by M2 proteins (Slepushkin et al., 1995). Neirynck et al. (1999) used a 23-aa long M2 transmembrane domain as an amino terminal fusion partner with the hepatitis B virus core antigen (HBcAg) to expose the M2 epitope(s) on the surface of HBcAg capsid-like particles. However, in spite of the fact that both full-length M2 protein and M2-HBcAg VLP induced detectable antibodies and protection in mice, it was unlikely that future influenza vaccines would be based exclusively on the M2 protein, as the M2 protein was present at low copy number per virion, was weakly antigenic, was unable to elicit antibodies that bound free influenza virions, and was unable to block virus attachment to cell receptors (i.e. virus neutralization).

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as virus-like particles (VLPs). Further, the particle with these influenza antigens may display conformational epitopes that elicit neutralizing antibodies to multiple strains of influenza viruses.

Several studies have demonstrated that recombinant influenza proteins could self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) demonstrated that efficient formation of influenza VLP depends on the expression levels of viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

SUMMARY OF INVENTION

According to the present invention, macromolecular protein structures are provided that comprise avian influenza virus type A H9N2 coding sequences for HA (GenBank Accession No. AJ404626), NA (GenBank Accession No. AJ404629), M1 (GenBank Accession No. AJ278646), M2 (GenBank Accession No. AF255363), and NP (GenBank Accession No. AF255742) proteins and that comprise human influenza virus type A H3N2 coding sequences for HA (GenBank Accession No. AJ311466) and for NA (GenBank Accession No. AJ291403). The genomic RNA encoding these influenza viral genes may be isolated from influenza virus isolates or from tissues of influenza-infected organisms. Each of these coding sequences from the same or different strains or types of influenza virus is cloned downstream of transcriptional promoters within expression vectors and are expressed in cells.

Thus, the invention provides a macromolecular protein structure containing (a) a first influenza virus M1 protein and (b) an additional structural protein, which may include a second or more influenza virus M1 protein; a first, second or more influenza virus HA protein; a first, second, or more influenza virus NA protein; and a first, second, or more influenza virus M2 protein. If the additional structural protein is not from a second or more influenza virus M1 protein, then both or all members of the group, e.g., first and second influenza M2 virus proteins are included. As such, there is provided a functional influenza protein structure, including a subviral particle, VLP, or capsomer structure, or a portion thereof, a vaccine, a multivalent vaccine, and mixtures thereof consisting essentially of influenza virus structural proteins produced by the method of the invention. In a particularly preferred embodiment, the influenza macromolecular protein structure includes influenza virus HA, NA, and M1 proteins that are the expression products of influenza virus genes cloned as synthetic fragments from a wild type virus.

The macromolecular protein structure may also include an additional structural protein, for example, a nucleoprotein (NP), membrane proteins from species other than noninfluenza viruses and a membrane protein from a non-influenza source, which are derived from avian or mammalian origins and different subtypes of influenza virus, including subtype A and B influenza viruses. The invention may include a chimeric macromolecular protein structure, which includes a portion of at least one protein having a moiety not produced by influenza virus.

Prevention of influenza may be accomplished by providing a macromolecular protein structure that may be self-assembled in a host cell from a recombinant construct. The macromolecular protein structure of the invention has the ability to self-assemble into homotypic or heterotypic virus-like particles (VLPs) that display conformational epitopes on HA and NA proteins, which elicit neutralizing antibodies that are protective. The composition may be a vaccine composition, which also contains a carrier or diluent and/or an adjuvant. The functional influenza VLPs elicit neutralizing antibodies against one or more strains or types of influenza virus depending on whether the functional influenza VLPs contain HA and/or NA proteins from one or more viral strains or types. The vaccine may include influenza virus proteins that are wild type influenza virus proteins. Preferably, the structural proteins containing the influenza VLP, or a portion of thereof, may be derived from the various strains of wild type influenza viruses. The influenza vaccines may be administered to humans or animals to elicit protective immunity against one or more strains or types of influenza virus.

The macromolecular protein structures of the invention may exhibit hemagglutinin activity and/or neuraminidase activity.

The invention provides a method for producing a VLP derived from influenza by constructing a recombinant construct that encodes influenza structural genes, including M1, HA, and at least one structural protein derived from influenza virus. A recombinant construct is used to transfect, infect, or transform a suitable host cell with the recombinant baculovirus. The host cell is cultured under conditions which permit the expression of M1, HA and at least one structural protein derived from influenza virus and the VLP is formed in the host cell. The infected cell media containing a functional influenza VLP is harvested and the VLP is purified. The invention also features an additional step of co-transfecting, co-infecting or co-transforming the host cell with a second recombinant construct which encodes a second influenza protein, thereby incorporating the second influenza protein within the VLP. Such structural proteins may be derived from influenza virus, including NA, M2, and NP, and at least one structural protein is derived from avian or mammalian origins. The structural protein may be a subtype A and B influenza viruses. According to the invention, the host cell may be a eukaryotic cell. In addition, the VLP may be a chimeric VLP.

The invention also features a method of formulating a drug substance containing an influenza VLP by introducing recombinant constructs encoding influenza viral genes into host cells and allowing self-assembly of the recombinant influenza viral proteins into a functional homotypic or heterotypic VLP in cells. The influenza VLP is isolated and purified and a drug substance is formulated containing the influenza VLP. The drug substance may further include an adjuvant. In addition, the invention provides a method for formulating a drug product, by mixing such a drug substance containing an influenza VLP with a lipid vesicle, i.e., a non-ionic lipid vesicle. Thus, functional homotypic or heterotypic VLPs may bud as enveloped particles from the infected cells.

The budded influenza VLPs may be isolated and purified by ultracentrifugation or column chromatography as drug substances and formulated alone or with adjuvants such as Novasomes®, a product of Novavax, Inc., as drug products such as vaccines. Novasomes®, which provide an enhanced immunological effect, are further described in U.S. Pat. No. 4,911,928, which is incorporated herein by reference.

The invention provides a method for detecting humoral immunity to influenza virus infection in a vertebrate by providing a test reagent including an effective antibody-detecting amount of influenza virus protein having at least one conformational epitope of an influenza virus macromolecular structure. The test reagent is contacted with a sample of bodily fluid from a vertebrate to be examined for influenza virus infection. Influenza virus specific antibodies contained in the sample are allowed to bind to the conformational epitope of an influenza virus macromolecular structure to form antigen-antibody complexes. The complexes are separated from unbound complexes and contacted with a detectably labeled immunoglobulin-binding agent. The amount of the detectably labeled immunoglobulin-binding agent that is bound to the complexes is determined.

Influenza virus may be detected in a specimen from an animal or human suspected of being infected with the virus by providing antibodies, which have a detectable signal producing label, or are attached to a detectably labeled reagent, having specificity to at least one conformational epitope of the particle of the influenza virus. The specimen is contacted with antibodies and the antibodies are allowed to bind to the influenza virus. The presence of influenza virus in the specimen is determined by means of the detectable label.

The invention provides methods for treatment, prevention, and generating a protective immune response by administering to a vertebrate an effective amount of the composition of the invention.

Alternatively, the influenza VLP drug substance may be formulated as laboratory reagents used for influenza virus structure studies and clinical diagnostic assays. The invention also provides a kit for treating influenza virus by administering an effective amount of a composition of the invention and directions for use.

BRIEF DESCRIPTION OF THE DRAWING

FIG. 1 depicts the nucleotide sequence of avian influenza A/Hong Kong/1073/99 (H9N2) virus neuraminidase (NA) gene (SEQ ID NO:1).

FIG. 2 depicts the nucleotide sequence of avian influenza A/Hong Kong/1073/99 (H9N2) virus hemagglutinin (HA) gene (SEQ ID NO:2).

FIG. 3 depicts the nucleotide sequence of avian influenza A/Hong Kong/1073/99 (H9N2) virus matrix protein M1 (M1) gene (SEQ ID NO:3).

FIG. 4 depicts the transfer vectors for construction of recombinant baculoviruses for expression of avian influenza A/Hong Kong/1073/99 (H9N2) HA, NA, and M1 proteins. FIG. 4A depicts a transfer vector for expression of individual genes and FIG. 4B depicts the transfer vector for multi-expression of the genes.

FIG. 5 depicts the expression of avian influenza A/Hong Kong/1073/99 (H9N2) virus HA, NA, and M1 proteins in Sf-9S cells.

FIG. 6 depicts the purification of avian influenza A/Hong Kong/1073/99 (H9N2) VLPs by the sucrose density gradient method.

FIG. 7 depicts the detection of influenza virus protein by gel filtration chromatography. The antibodies used in the Western blot analyses are as follows: (A) rabbit anti-H9N2; (b) murine anti-M1 mAb; and (C) murine anti-BACgp64.

FIG. 8 depicts the detection of avian influenza A/Hong Kong/1073/99 (H9N2) proteins including subviral particles, VLP, and VLP complexes, by electron microscopy.

FIG. 9 depicts the hemagglutination activity of purified avian influenza A/Hong Kong/1073/99 (H9N2) VLPs.

FIG. 10 depicts the neuraminidase activity of purified avian influenza A/Hong Kong/1073/99 (H9N2) VLPs.

FIG. 11 depicts the immunization and bleed schedule for the immunogenicity study of recombinant influenza with purified avian influenza A/Hong Kong/1073/99 (H9N2) VLPs in mice.

FIG. 12 depicts the results of an immunogenicity study in mice immunized with recombinant influenza H9N2 VLPs. FIG. 12A depicts sera from BALB/c mice immunized with recombinant VLPs comprised of HA, NA, and M1 proteins from avian influenza virus type A/H9N2/Hong Kong/1073/ 99. FIG. 12B depicts sera from New Zealand white rabbits immunized with inactivated avian influenza virus type A H9N2 were reacted with Western blots containing inactivated avian influenza virus type A H9N2 (lanes 1 and 3) or cold-adapted avian influenza virus type A H9N2 (lanes 2 and 4).

DETAILED DESCRIPTION OF THE INVENTION

As used herein, the term "baculovius," also known as baculoviridae, refers to a family of enveloped DNA viruses of arthropods, members of which may be used as expression vectors for producing recombinant proteins in insert cell cultures. The virion contains one or more rod-shaped nucleocapsids containing a molecule of circular supercoiled double-stranded DNA ($M_r$ $54\times10^6$-$154\times10^6$). The virus used as a vector is generally *Autographa californica* nuclear polyhedrosis virus (NVP). Expression of introduced genes is under the control of the strong promoter that normally regulates expression of the polyhedron protein component of the large nuclear inclusion in which the viruses are embedded in the infected cells.

As used herein, the term "derived from" refers to the origin or source, and may include naturally occurring, recombinant, unpurified, or purified molecules. The proteins and molecules of the present invention may be derived from influenza or non-influenza molecules.

As used herein the term "first" influenza virus protein, i.e., a first influenza virus MI protein, refers to a protein, such as M1, HA, NA, and M2, that is derived from a particular strain of influenza virus. The strain or type of the first influenza virus differs from the strain or type of the second influenza virus protein. Thus, "second" influenza virus protein, i.e., the second influenza virus M1 protein, refers to a protein, such as M1, HA, NA, and M2, that is derived from a second strain of influenza virus, which is a different strain or type than the first influenza virus protein.

As used herein, the term "hemagglutinin activity" refers to the ability of HA-containing proteins, VLPs, or portions thereof to bind and agglutinate red blood cells (erythrocytes).

As used herein, the term "neuraminidase activity" refers to the enzymatic activity of NA-containing proteins, VLPs, or portions thereof to cleave sialic acid residues from substrates including proteins such as fetuin.

As used herein, the term "heterotypic" refers to one or more different types or strains of virus.

As used herein, the term "homotypic" refers to one type or strain of virus.

As used herein, the term "macromolecular protein structure" refers to the construction or arrangement of one or more proteins.

As used herein, the term "multivalent" vaccine refers to a vaccine against multiple types or strains of influenza virus.

As used herein, the term "non-influenza" refers to a protein or molecule that is not derived from influenza virus.

As used herein, the term "vaccine" refers to a preparation of dead or weakened pathogens, or of derived antigenic determinants, that is used to induce formation of antibodies or immunity against the pathogen. A vaccine given to provide immunity to the disease, for example, influenza, which is caused by influenza viruses. The present invention provides vaccine compositions that are immunogenic and provide protection.

Influenza remains a pervasive public health concern despite the availability of specific inactivated virus vaccines that are 60-80% effective under optimal conditions. When these vaccines are effective, illness is usually averted by preventing viral infection. Vaccine failure can occur as a result of accumulated antigenic differences (antigenic shift and antigenic drift). For example, avian influenza virus type A H9N2 co-circulated with human influenza virus type A Sydney/97 H3N2 in pigs and led to genetic reassortment and emergence of new strains of human influenza virus with pandemic potential (Peiris et al., 2001). In the event of such antigenic shift, it is unlikely that current vaccines would provide adequate protection.

Another reason for the paucity of influenza vaccine programs is the relatively short persistence of immunity elicited by the current vaccines. Further inadequacy of influenza control measures reflects restricted use of current vaccines because of vaccine reactogenicity and side effects in young children, elderly, and people with allergies to components of eggs, which are used in manufacturing of commercially licensed inactivated virus influenza vaccines.

Additionally, inactivated influenza virus vaccines often lack or contain altered HA and NA conformational epitopes, which elicit neutralizing antibodies and play a major role in protection against disease. Thus, inactivated viral vaccines, as well as some recombinant monomeric influenza subunit protein vaccines, deliver inadequate protection. On the other hand, macromolecular protein structures, such as capsomers, subviral particles, and/or VLPs, include multiple copies of native proteins exhibiting conformational epitopes, which are advantageous for optimal vaccine immunogenicity.

The present invention describes the cloning of avian influenza A/Hong Kong/1073/99 (H9N2) virus HA, NA, and M1 genes into a single baculovirus expression vector alone or in tandem and production of influenza vaccine candidates or reagents comprised of recombinant influenza structural proteins that self-assemble into functional and immunogenic homotypic macromolecular protein structures, including subviral influenza particles and influenza VLP, in baculovirus-infected insect cells.

The present invention further features the cloning of human influenza A/Sydney/5/94 (H3N2) virus HA, NA, M1, M2, and NP genes into baculovirus expression vectors and production influenza vaccine candidates or reagents comprised of influenza structural proteins that self-assemble into functional and immunogenic homotypic macromolecular protein structures, including subviral influenza particles and influenza VLP, in baculovirus-infected insect cells.

In addition, the instant invention describes the cloning of the HA gene of human influenza A/Sydney/5/94 (H3N2) virus and the HA, NA, and M1 genes of avian influenza A/Hong Kong/1073/99 (H9N2) into a single baculovirus expression vector in tandem and production influenza vaccine candidates or reagents comprised of influenza structural proteins that self-assemble into functional and immunogenic heterotypic macromolecular protein structures, including subviral influenza particles and influenza VLP, in baculovirus-infected insect cells.

This invention is further illustrated by the following examples which should not be construed as limiting. The contents of all references, patents and published patent applications cited throughout this application, as well as the Figures and the Sequence Listing, are incorporated herein by reference.

SPECIFIC EXAMPLES

Example 1

Materials and Methods

Avian influenza A/Hong Kong/1073/99 (H9N2) virus HA, NA, and M1 genes were expressed in *Spodoptera frugiperda* cells (Sf-9S cell line; ATCC PTA-4047) using the baculovirus bacmid expression system. The HA, NA, and M1 genes were synthesized by the reverse transcription and polymerase chain reaction (PCR) using RNA isolated from avian influenza A/Hong Kong/1073/99 (H9N2) virus (FIGS. 1, 2, and 3). For reverse transcription and PCR, oligonucleotide primers specific for avian influenza A/Hong Kong/1073/99 (H9N2) virus HA, NA, and M1 genes were used (Table 1). The cDNA copies of these genes were cloned initially into the bacterial subcloning vector, pCR2.1TOPO. From the resulting three pCR2.1TOPO-based plasmids, the HA, NA, and M1 genes were inserted downstream of the AcMNPV polyhedrin promoters in the baculovirus transfer vector, pFastBac1 (InVitrogen), resulting in three pFastBac1-based plasmids: pHA, pNA, and pM1 expressing these influenza virus genes, respectively. Then, a single pFastBac1-based plasmid pHAM was constructed encoding both the HA and M1 genes, each downstream from a separate polyhedrin promoter (FIG. 4). The nucleotide sequence of the NA gene with the adjacent 5'- and 3'-regions within the pNA plasmid was determined (SEQ ID NO:1)(FIG. 1). At the same time, the nucleotide sequences of the HA and M1 genes with the adjacent regions were also determined using the pHAM plasmid (SEQ ID NOS:2 and 3)(FIGS. 2 and 3).

Finally, a restriction DNA fragment from the pHAM plasmid that encoded both the HA and M1 expression cassettes was cloned into the pNA plasmid. This resulted in the plasmid pNAHAM encoding avian influenza A/Hong Kong/1073/99 (H9N2) virus HA, NA, and M1 genes (FIG. 4).

Plasmid pNAHAM was used to construct a recombinant baculovirus containing influenza virus NA, HA, and M1 genes integrated into the genome, each downstream from a separate baculovirus polyhedrin promoter. Infection of permissive Sf-9S insect cells with the resulting recombinant baculovirus resulted in co-expression of these three influenza genes in each Sf-9S cell infected with such recombinant baculovirus.

Results

The expression products in infected Sf-9S cells were characterized at 72 hr postinfection (p.i.) by SDS-PAGE analysis, Coomassie blue protein staining, and Western immunoblot analysis using HA- and M1-specific antibodies (FIG. 5). Western immunoblot analysis was carried out using rabbit antibody raised against influenza virus type A/Hong Kong/1073/99 (H9N2)(CDC, Atlanta, Ga., USA), or mouse monoclonal antibody to influenza M1 protein (Serotec, UK). The HA, NA, and M1 proteins of the expected molecular weights (64 kd, 60 kd, and 31 kd, respectively) were detected by Western immunoblot analysis. Compared to the amount of HA protein detected in this assay, the NA protein showed lower reactivity with rabbit serum to influenza A/Hong Kong/ 1073/99 (H9N2) virus. Explanations for the amount of detectable NA protein included lower expression levels of the NA protein from Sf-9S cells infected with recombinant baculovirus as compared to the HA protein, lower reactivity of the NA with this serum under denaturing conditions in the Western immunoblot assay (due to the elimination of important NA epitopes during gel electrophoresis of membrane binding), lower NA-antibody avidity as compared to HA-antibody, or a lower abundance of NA-antibodies in the serum.

The culture medium from the Sf-9S cells infected with recombinant baculovirus expressing A/Hong Kong/1073/99 (H9N2) HA, NA, and M1 proteins was also probed for influenza proteins. The clarified culture supernatants were subjected to ultracentrifugation at 27,000 rpm in order to concentrate high-molecular protein complexes of influenza virus, such as subviral particles, VLP, complexes of VLP, and possibly, other self-assembled particulates comprised of influenza HA, NA, and M1 proteins. Pelleted protein products were resuspended in phosphate-buffered saline (PBS, pH 7.2) and further purified by ultracentrifugation on discontinuous 20-60% sucrose step gradients. Fractions from the sucrose gradients were collected and analyzed by SDS-PAGE analysis, Western immunoblot analysis, and electron microscopy.

Figure 6:
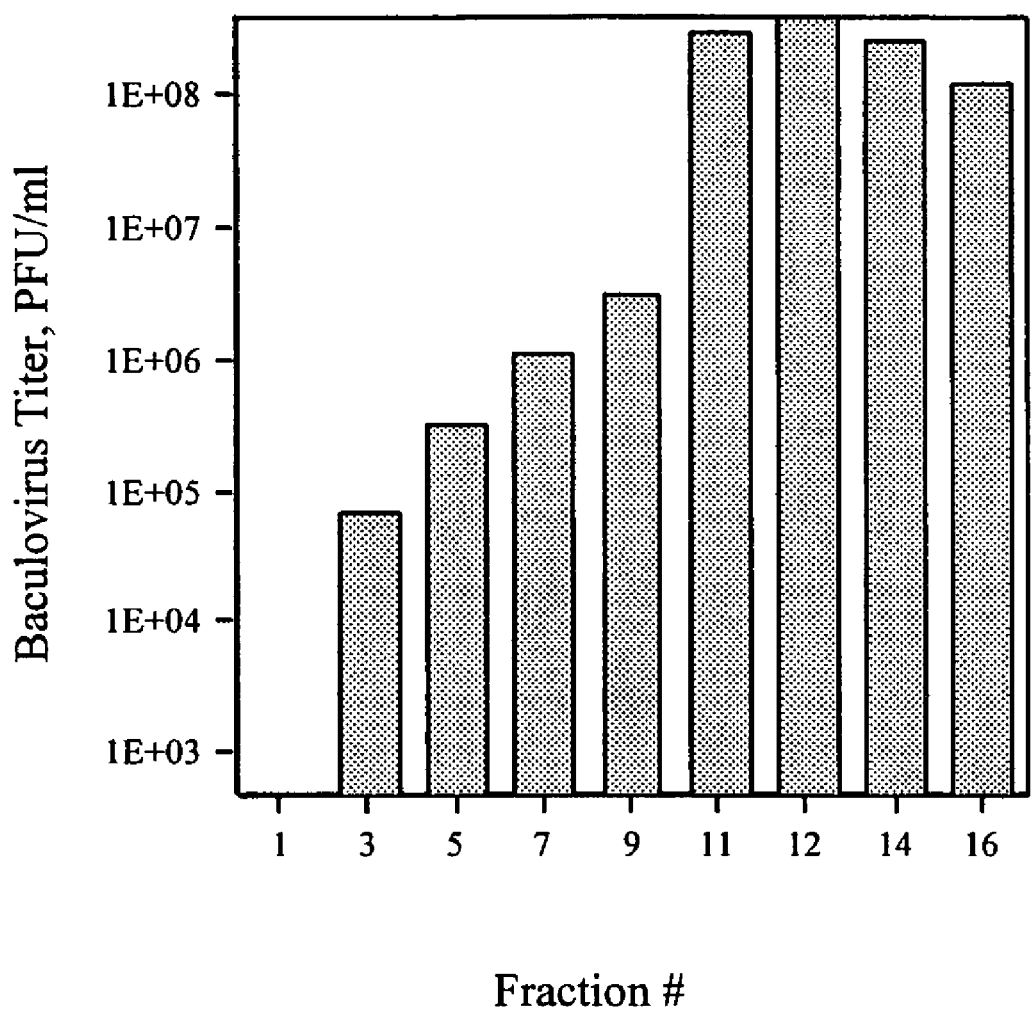

Influenza HA and M1 proteins of the expected molecular weights were detected in multiple sucrose density gradient fractions by Coomassie blue staining and Western immunoblot analysis (FIG. 6). This suggested that influenza viral proteins from infected Sf-9S cells are aggregated in complexes of high-molecular weight, such as capsomers, subviral particles, VLP, and/or VLP complexes. The NA proteins, although inconsistently detected by Coomassie blue staining and Western immunoblot analysis, which was likely due to the inability of the rabbit anti-influenza serum to recognize denatured NA protein in the Western immunoblot assay, were consistently detected in neuraminidase enzyme activity assay (FIG. 10).

The presence of high-molecular VLPs was confirmed by gel filtration chromatography. An aliquot from sucrose density gradient fractions containing influenza viral proteins was loaded onto a Sepharose CL-4B column for fractionation based on mass. The column was calibrated with dextran blue 2000, dextran yellow, and vitamin B12 (Amersham Pharmacia) with apparent molecular weights of 2,000,000; 20,000; and 1,357 daltons, respectively, and the void volume of the column was determined. As expected, high-molecular influenza viral proteins migrated in the void volume of the column, which was characteristic of macromolecular proteins, such as virus particles. Fractions were analyzed by Western immunoblot analysis to detect influenza and baculovirus proteins. For example, M1 proteins were detected in the void volume fractions, which also contained baculovirus proteins (FIG. 7).

Figure 8:
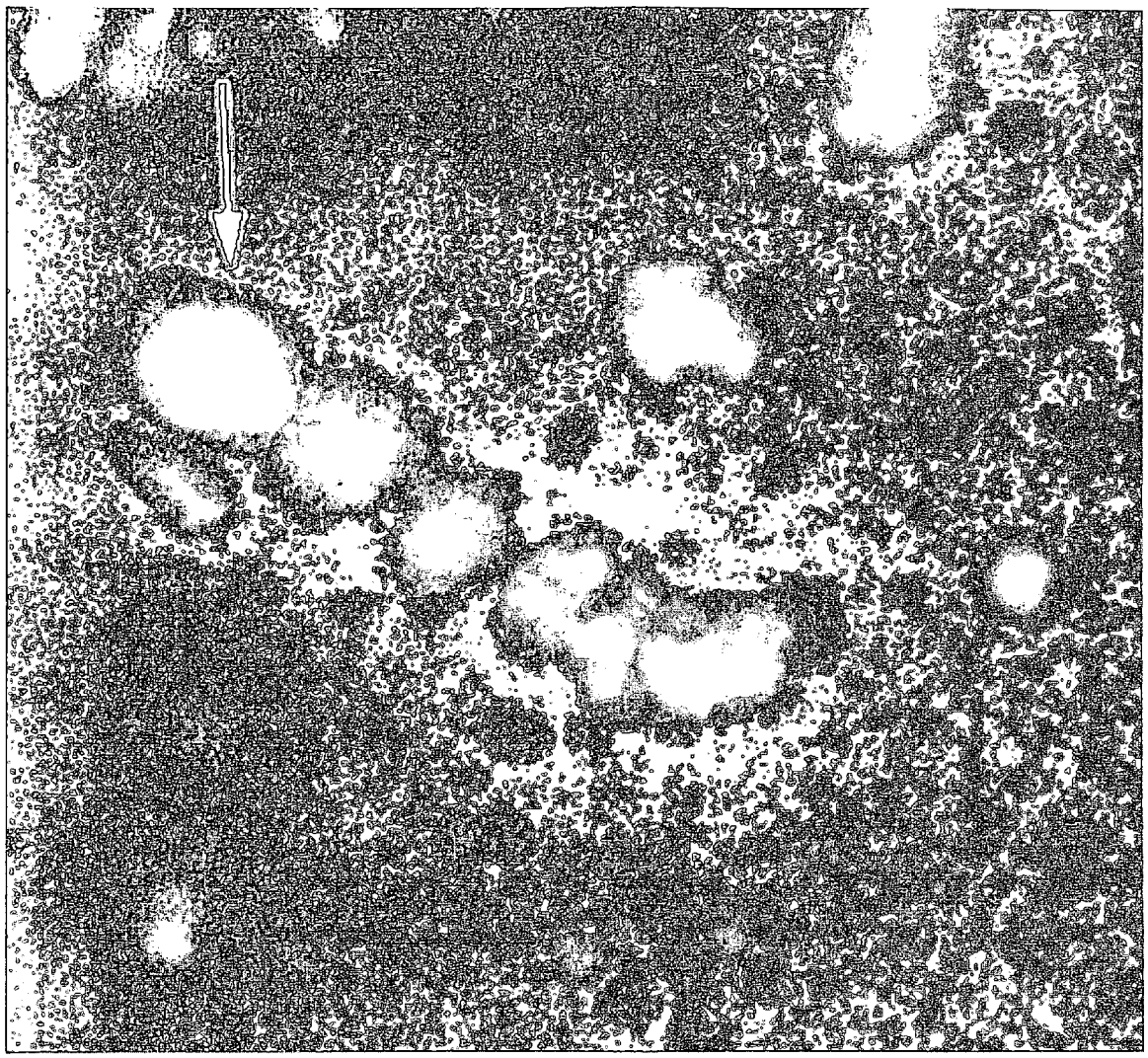

The morphology of influenza VLPs and proteins in sucrose gradient fractions was elucidated by electron microscopy. For negative-staining electron microscopy, influenza proteins from two sucrose density gradient fractions were fixed with 2% glutaraldehyde in PBS, pH 7.2. Electron microscopic examination of negatively-stained samples revealed the presence of macromolecular protein complexes or VLPs in both fractions. These VLPs displayed different sizes including diameters of approximately 60 and 80 nm and morphologies (spheres). Larger complexes of both types of particles were also detected, as well as rod-shaped particles (FIG. 8). All observed macromolecular structures had spikes (peplomers) on their surfaces, which is characteristic of influenza viruses. Since the size and appearance of 80 nm particles was similar to particles of wild type influenza virus, these structures likely represented VLPs, which have distinct similarities to wild type influenza virions, including similar particle geometry, architecture, triangulation number, symmetry, and other characteristics. The smaller particles of approximately 60 nm may represent subviral particles that differ from VLPs both morphologically and structurally. Similar phenomenon of recombinant macromolecular proteins of different sizes and morphologies was also reported for other viruses. For example, recombinant core antigen (HBcAg) of hepatitis B virus forms particles of different sizes, which have different architecture and triangulation number $T=4$ and $T=3$, respectively (Crowther et al., 1994).

Figure 9:
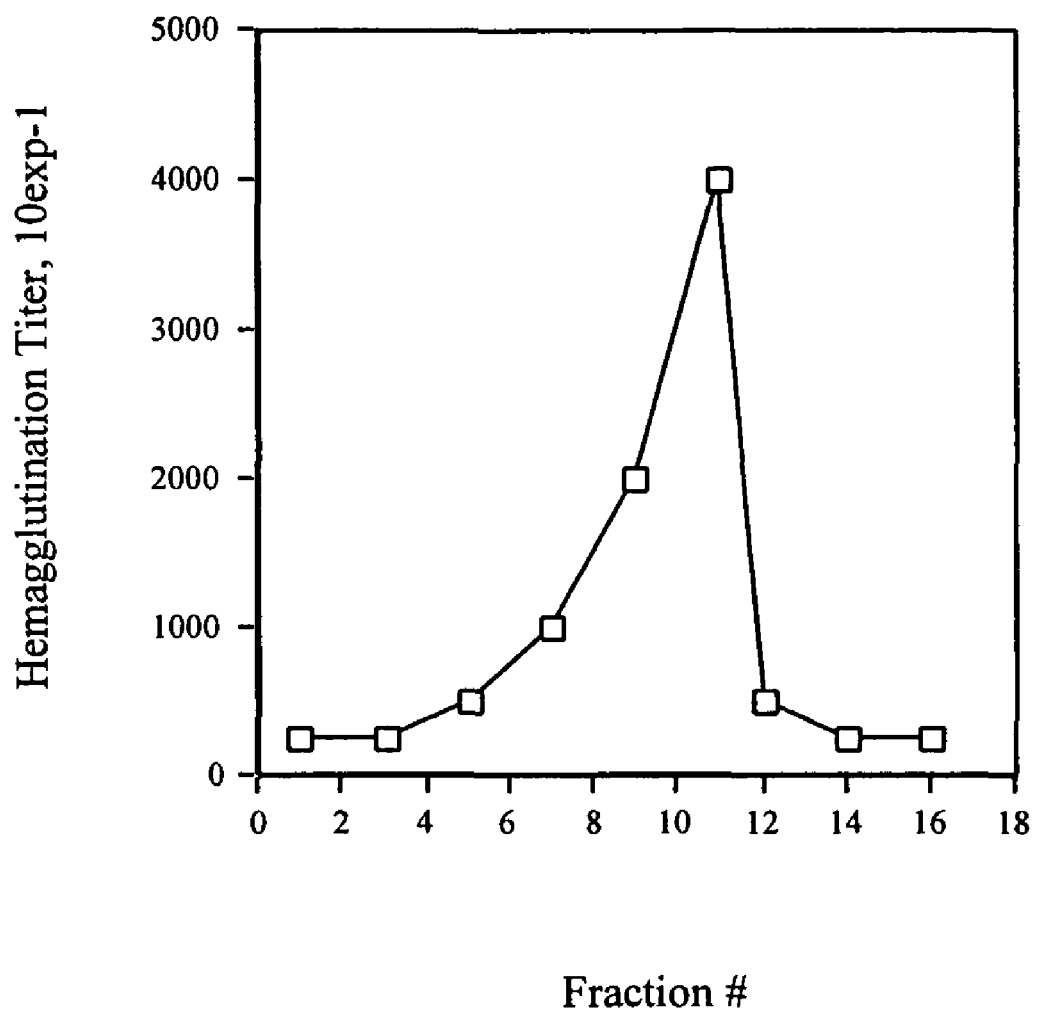
Figure 10:
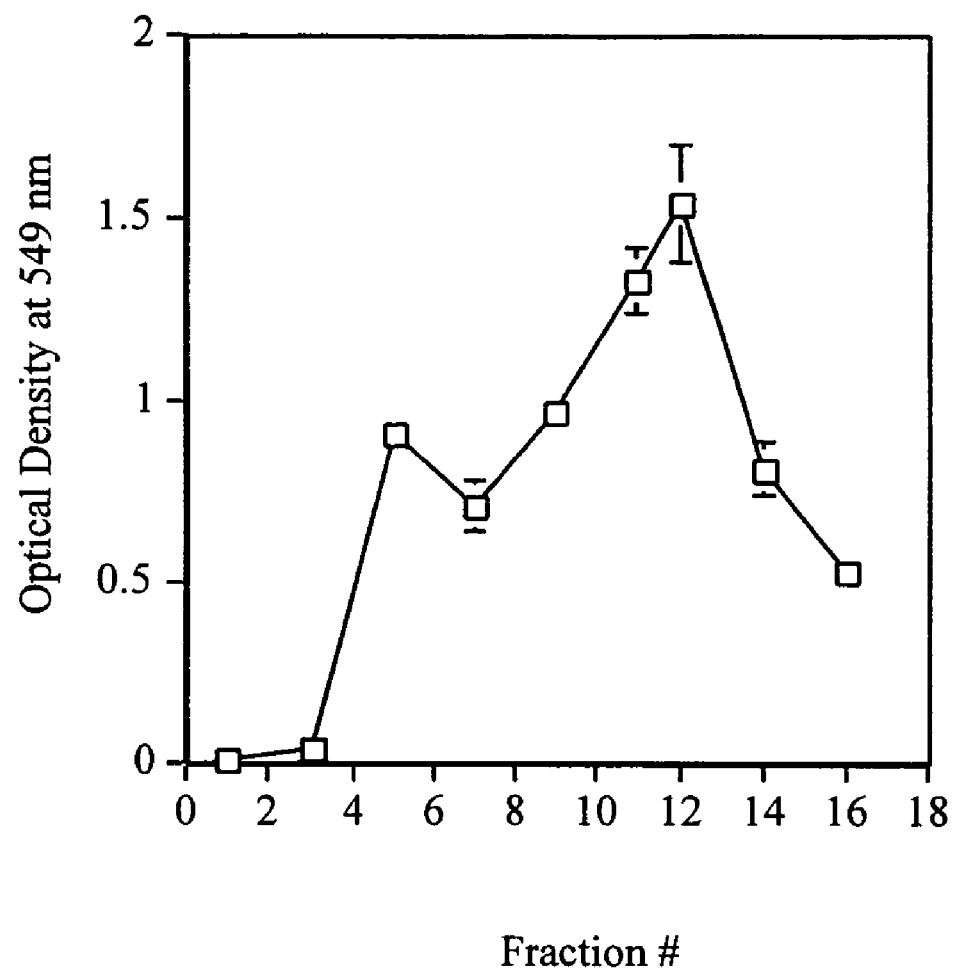

To characterize the functional properties of the purified influenza A/Hong Kong/1073/99 (H9N2) VLPs, samples were tested in a hemagglutination assay (FIG. 9) and a neuraminidase enzyme assay (FIG. 10). For the hemagglutination assay, 2-fold dilutions of purified influenza VLPs were mixed with 0.6% guinea pig red blood cells and incubated at 4° C. for 1 hr or 16 hr. The extent of hemagglutination was inspected visually and the highest dilution of recombinant influenza proteins capable of agglutinating red blood cells was determined and recorded (FIG. 9). Again, many fractions from the sucrose density gradient exhibited hemagglutination activity, suggesting that multiple macromolecular and monomeric forms of influenza proteins were present. The highest titer detected was 1:4000. In a control experiment, wild-type influenza A/Shangdong virus demonstrated a titer of 1:2000. The hemagglutination assay revealed that the recombinant VLPs consisting of influenza A/Hong Kong/1073/99 (H9N2) virus HA, NA, and M1 proteins were functionally active. This suggested that the assembly, conformation, and folding of the HA subunit proteins within the VLPs were similar or identical to that of the wild type influenza virus.

Additionally, a neuraminidase enzyme assay was performed on samples of purified H9N2 VLPs. The amount of neuraminidase activity in sucrose density gradient fractions was determined using fetuin as a substrate. In the neuraminidase assay, the neuraminidase cleaved sialic acid from substrate molecules to release sialic acid for measurement. Arsenite reagent was added to stop enzyme activity. The amount of sialic acid liberated was determined chemically with thiobarbituric acid that produces a pink color that was proportional to the amount of free sialic acid. The amount of color (chromophor) was measured spectrophotometrically at wavelength 549 nm. Using this method, neuraminidase activity was demonstrated in sucrose gradient fractions containing influenza VLPs (FIG. 10). As expected, the activity was observed in several fractions, with two peak fractions. As a positive control, wild type influenza virus was used. The wild type influenza virus exhibited neuraminidase enzyme activity comparable to that of purified influenza VLPs. These findings corroborated the HA results with regard to-protein conformation and suggested that purified VLPs of influenza A/Hong Kong/1073/99 (H9N2) virus were functionally similar to wild type influenza virus.

The results from the above analyses and assays indicated that expression of influenza A/Hong Kong/1073/99 (H9N2) HA, NA, and M1 proteins was sufficient for the self-assembly and transport of functional VLPs from baculovirus-infected insect cells. Since these influenza VLPs represented self-assembled influenza structural proteins and demonstrated functional and biochemical properties similar to those of wild type influenza virus, these influenza VLPs conserved important structural conformations including surface epitopes necessary for effective influenza vaccines.

Example 2

RT-PCR Cloning of Avian Influenza A/Hong Kong/1073/99 Viral Genes

It is an object of the present invention to provide synthetic nucleic acid sequences capable of directing production of recombinant influenza virus proteins. Such synthetic nucleic acid sequences were obtained by reverse transcription and polymerase chain reaction (PCR) methods using influenza virus natural genomic RNA isolated from the virus. For the purpose of this application, nucleic acid sequence refers to RNA, DNA, cDNA or any synthetic variant thereof which encodes the protein.

Avian influenza A/Hong Kong/1073/99 (H9N2) virus was provided by Dr. K. Subbarao (Centers for Disease Control, Atlanta, Ga., USA). Viral genomic RNA was isolated by the acid phenol RNA extraction method under Biosafety Level 3 (BSL3) containment conditions at CDC using Trizol LS reagent (Invitrogen, Carlsbad, Calif. USA). cDNA molecules of the viral RNAs were obtained by reverse transcription using MuLV reverse transcriptase (InVitrogen) and PCR using oligonucleotide primers specific for HA, NA, and M1 proteins and Taq I DNA polymerase (InVitrogen)(Table 1). The PCR fragments were cloned into the bacterial subcloning vector, pCR2.1TOPO (InVitrogen), between Eco RI sites that resulted in three recombinant plasmids, containing the HA, NA, and M1 cDNA clones.

Example 3

RT-PCR Cloning of Human Influenza A/Sydney/5/94 (H3N2) Viral Genes

Influenza A/Sydney/5/94 (H3N2) virus was obtained from Dr. M. Massare (Novavax, Inc., Rockville, Md.). Viral genomic RNA was isolated by the RNA acid phenol extraction method under BSL2 containment conditions at Novavax, Inc. using Trizol LS reagent (Invitrogen). cDNA molecules of the viral RNAs were obtained by reverse transcription and PCR using oligonucleotide primers specific for HA, NA, M1, M2, and NP proteins (Table 2). The PCR fragments were cloned into the bacterial subcloning vector, pCR2.1TOPO, between Eco RI sites that resulted in five recombinant plasmids, containing the HA, NA, M1, M2, and NP cDNA clones.

Example 4

Cloning of Avian Influenza A/Hong Kong/1073/99 Viral cDNAs into baculovirus Transfer Vectors From the pCR2.1TOPO-based plasmids, the HA, NA, or M1 genes were subcloned into pFastBac1 baculovirus transfer vector (InVitrogen) within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-HA was inserted into Bam HI-Kpn I digested pFastBac1 plasmid DNA. For the NA gene, an Eco RI DNA fragment from pCR2.1TOPO-NA was inserted into Eco RI digested pFastBac1 plasmid DNA. For the M1 gene, an Eco RI DNA fragment from pCR2.1TOPO-M1 was inserted into Eco RI digested pFastBac1 plasmid DNA. Competent *E. coli* DH5α_bacteria (InVitrogen) were transformed with these DNA ligation reactions, transformed colonies resulted, and bacterial clones isolated. The resulting pFastBac1-based plasmids, pFastBac1-HA, pFastBac1-NA, and pFastBac1-M1 were characterized by restriction enzyme mapping on agarose gels (FIG. 4A). The nucleotide sequences as shown on FIGS. 1-3 of the cloned genes were determined by automated DNA sequencing. DNA sequence analysis showed that the cloned influenza HA, NA, and M1 genes were identical to the nucleotide sequences for these genes as published previously [NA, HA, and M1 genes of influenza A/Hong Kong/1073/99 (H9N2)(GenBank accession numbers AJ404629, AJ404626, and AJ278646, respectively)].

Example 5

Cloning of Human Influenza A/Sydney/5/94 Viral cDNAs into Baculovirus Transfer Vectors From the pCR2.1TOPO-based plasmids, the HA, NA, M1, M2, and NP genes were subcloned into pFastBac1 baculovirus transfer vector within the polyhedron locus and Tn7 att sites and downstream of the baculovirus polyhedrin promoter and upstream of the polyadenylation signal sequence. The viral genes were ligated with T4 DNA ligase. For the HA gene, a Bam HI-Kpn I DNA fragment from pCR2.1TOPO-hHA3 was inserted into Bam HI-Kpn I digested pFastBac1 plasmid DNA. For the NA gene, an Eco RI DNA fragment from pCR2.1TOPO-hNA was inserted into Eco RI digested pFastBac1 plasmid DNA. For the M1 gene, an Eco RI DNA fragment from pCR2.1TOPO-hM1 was inserted into Eco RI digested pFastBac1 plasmid DNA. For the M2 gene, an Eco RI DNA fragment from pCR2.1TOPO-hM2 was inserted into Eco RI digested pFastBac1 plasmid DNA. For the NP gene, an Eco RI DNA fragment from pCR2.1TOPO-hNP was inserted into Eco RI digested pFastBac1 plasmid DNA. Competent *E. coli* DH5α_bacteria were transformed with these DNA ligation reactions, transformed colonies resulted, and bacterial clones isolated. The resulting pFastBac1-based plasmids, pFastBac1-hHA3, pFastBac1-hNA2, pFastBac1-hM1, pFASTBAC1-hM2, and pFASTBAC1-hNP were characterized by restriction enzyme mapping on agarose gels. The nucleotide sequences of the cloned genes were determined by automated DNA sequencing. DNA sequence analysis showed that the cloned influenza HA, NA, M1, M2, and NP genes were identical to the nucleotide sequences for these genes as published previously.

Example 6

Construction of Multigenic Baculovirus Transfer Vectors Encoding Multiple Avian Influenza A/Hong Kong/1073/99 Viral Genes In order to construct pFastBac1-based bacmid transfer vectors expressing multiple influenza A/Hong Kong/1073/99 (H9N2) virus genes, initially a Sna BI-Hpa I DNA fragment from pFastBac1-M1 plasmid containing the M1 gene was cloned into Hpa I site of pFastBac 1-HA. This resulted in pFastBac1-HAM plasmid encoding both HA and M1 genes within independent expression cassettes and expressed under the control of separate polyhedrin promoters.

Finally, a Sna BI-Avr II DNA fragment from pFastBac1-HAM containing the HA and M1 expression cassettes, was transferred into Hpa I-Avr II digested pFastBac1-NA plasmid DNA. This resulted in the plasmid pFastBac1-NAHAM encoding three independent expression cassettes for expression of influenza HA, NA, and M1 genes and expressed under the control of separate polyhedrin promoters (FIG. 4B).

In another example, the H3 gene from pFASTBAC1-hHA3 (see Example 5) was cloned into pFASTBAC1-NAHAM as a fourth influenza viral gene for the expression and production of heterotypic influenza VLPs.

Example 7

Generation of Multigenic Recombinant Baculovirus Encoding NA, HA, and M1 Genes of Avian Influenza A/Hong Kong/1073/99 Virus in Insect Cells The resulting multigenic bacmid transfer vector pFastBac1-NAHAM was used to generate a multigenic recombinant baculovirus encoding avian influenza A/Hong Kong/1073/99 (H9N2) HA, NA, and M1 genes for expression in insect cells. Recombinant bacmid DNAs were produced by site-specific recombination at polyhedrin and Tn7 att DNA sequences between pFastBac1-NAHAM DNA and the AcMNPC baculovirus genome harbored in competent *E. coli* DH10BAC cells (InVitrogen)(FIG. 4B). Recombinant bacmid DNA was isolated by the mini-prep plasmid DNA method and transfected into Sf-9s cells using the cationic lipid CELLFECTIN (InVitrogen). Following transfection, recombinant baculoviruses were isolated, plaque purified, and amplified in Sf-9S insect cells. Virus stocks were prepared in Sf-9S insect cells and characterized for expression of avian influenza viral HA, NA, and M1 gene products. The resulting recombinant baculovirus was designated bNAHAM-H9N2.

Example 8

Expression of Recombinant Avian Influenza A/Hong Kong/1073/99 Proteins in Insect Cells Sf-9S insect cells maintained as suspension cultures in shaker flasks at 28° C. in serum-free medium (HyQ SFM, HyClone, Ogden, Utah) were infected at a cell density of $2\times10^6$ cells/ml with the recombinant baculovirus, bNAHAM-H9N2, at a multiplicity of infection (MOI) of 3 pfu/cell. The virus infection proceeded for 72 hrs. to allow expression of influenza proteins. Expression of avian influenza A/Hong Kong/1073/99 (H9N2) HA and M1 proteins in infected insect cells was confirmed by SDS-PAGE and Western immunoblot analyses. SDS-PAGE analysis was performed on 4-12% linear gradient NuPAGE gels (Invitrogen) under reduced and denaturing conditions. Primary antibodies in Western immunoblot analysis were polyclonal rabbit antiserum raised against avian influenza A/Hong Kong/1073/99 (H9N2) obtained from CDC and monoclonal murine antiserum to influenza M1 protein (Serotec, UK). Secondary antibodies for Western immunoblot analysis were alkaline phosphatase conjugated goat IgG antisera raised against rabbit or mouse IgG (H+L) (Kirkegaard and Perry Laboratories, Gaithersburg, Md., USA). Results of these analyses (FIG. 5) indicated that the HA and M1 proteins were expressed in the baculovirus-infected insect cells.

Example 9

Purification of Recombinant Avian Influenza H9N2 Virus-Like Particles and Macromolecular Protein Complexes Culture supernatants (200 ml) from Sf-9S insect cells infected with the recombinant baculovirus bNAHAM-H9N2 that expressed avian influenza A/Hong Kong/1073/99 (H9N2) HA, NA, and M1 gene products were harvested by low speed centrifugation. Culture supernatants were clarified by centrifugation in a Sorval RC-5B superspeed centrifuge for 1 hr at 10,000×g and 4° C. using a GS-3 rotor. Virus and VLPs were isolated from clarified culture supernatants by centrifugation in a Sorval OTD-65 ultracentrifuge for 3 hr at 27,000 rpm and 4° C. using a Sorval TH-641 swinging bucket rotor. The virus pellet was resuspended in 1 ml of PBS (pH 7.2), loaded onto a 20-60% (w/v) discontinuous sucrose step gradient, and resolved by centrifugation in a Sorval OTD-65 ultracentrifuge for 16 hr at 27,000 rpm and 4° C. using a Sorval TH-641 rotor. Fractions (0.5 ml) were collected from the top of the sucrose gradient.

Influenza proteins in the sucrose gradient fractions were analyzed by SDS-PAGE and Western immunoblot analyses as described above in Example 6. The HA and M1 proteins were found in the same sucrose gradient fractions (FIG. 6) as shown by Western blot analysis and suggested that the HA and M1 proteins were associated as macromolecular protein complexes. Also the HA and M1 proteins were found in fractions throughout the sucrose gradient suggesting that these recombinant viral proteins were associated with macromolecular protein complexes of different densities and compositions.

Example 10

Analysis of Recombinant Avian Influenza H9N2 VLPs and Proteins by Gel Filtration Chromatography Protein macromolecules such as VLPs and monomeric proteins migrate differently on gel filtration or size exclusion chromatographic columns based on their mass size and shape. To determine whether the recombinant influenza proteins from sucrose gradient fractions were monomeric proteins or macromolecular protein complexes such as VLPs, a chromatography column (7 mm×140 mm) with a resin bed volume of 14 ml of Sepharose CL-4B (Amersham) was prepared. The size exclusion column was equilibrated with PBS and calibrated with Dextran Blue 2000, Dextran Yellow, and Vitamin B12 (Amersham Pharmacia) with apparent molecular weights of 2,000,000; 20,000; and 1,357, respectively, to ascertain the column void volume. Dextran Blue 2000 eluted from the column in the void volume (6 ml fraction). As expected, the recombinant influenza protein complexes eluted from the column in the void volume (6 ml fraction) also. This result was characteristic of a high molecular weight macromolecular protein complex such as VLPs. Viral proteins in the column fractions were detected by Western immunoblot analysis as described above in Example 6. The M1 proteins were detected in the void volume fractions (FIG. 7). As expected baculovirus proteins were also in the void volume.

Example 11

Electron Microscopy of Recombinant Influenza VLPs

To determine whether the macromolecular protein complexes isolated on sucrose gradients and containing recombinant avian influenza proteins had morphologies similar to influenza virions, electron microscopic examination of negatively stained samples was performed. Recombinant avian influenza A/Hong Kong/1073/99 (H9N2) protein complexes were concentrated and purified from culture supernatants by ultracentrifugation on discontinuous sucrose gradients as described in Example 7. Aliquots of the sucrose gradient fractions were treated with a 2% glutaraldehyde in PBS, pH7.2, absorbed onto fresh discharged plastic/carbon-coated grids, and washed with distilled water. The samples were stained with 2% sodium phosphotungstate, pH 6.5, and observed using a transmission electron microscope (Philips). Electron micrographs of negatively-stained samples of recombinant avian influenza H9N2 protein complexes from two sucrose gradient fractions showed spherical and rod-shaped particles (FIG. 8) from two sucrose gradient fractions. The particles had different sizes (60 and 80 nm) and morphologies. Larger complexes of both types of particles were also detected, as well as rod-shaped particles (FIG. 8). All observed protein complex structures exhibited spike like surface projections resembling influenza virus HA and NA peplomers. Since the size and appearance of the 80 nm particles was similar to that of wild type influenza virus particles, these structures likely represented enveloped influenza VLPs. The smaller particles of approximately 60 nm probably represented subviral particles that differed from the above VLPs both morphologically and structurally.

Example 12

Analysis of Functional Characteristics of Influenza Proteins by Hemagglutination Assay To determine whether the purified influenza VLPs and proteins possessed functional activities, such as hemagglutination and neuraminidase activity, which were characteristic for influenza virus, the purified influenza VLPs and proteins were tested in hemagglutination and neuraminidase assays.

For the hemagglutination assay, a series of 2-fold dilutions of sucrose gradient fractions containing influenza VLPs or positive control wild type influenza virus type A were prepared. Then they were mixed with 0.6% guinea pig red blood cells in PBS (pH 7.2) and incubated at 4° C. for 1 to 16 hr. As a negative control, PBS was used. The extent of hemagglutination was determined visually, and the highest dilution of fraction capable of agglutinating guinea pig red blood cells was determined (FIG. 9). The highest hemagglutination titer observed for the purified influenza VLPs and proteins was 1:4000, which was higher than the titer shown by the wild type influenza control, which was 1:2000.

Example 13

Analysis of Functional Characteristics of Influenza Proteins by Neuraminidase Assay The amount of neuraminidase activity in influenza VLP-containing sucrose gradient fractions was determined by the neuraminidase assay. In this assay the NA (an enzyme) acted on the substrate (fetuin) and released sialic acid. Arsenite reagent was added to stop enzyme activity. The amount of sialic acid liberated was determined chemically with the thiobarbituric acid that produced a pink color in proportion to free sialic acid. The amount of color (chromophor) was measured in a spectrophotometer at wavelength 594 nm. The data, as depicted in FIG. 8, showed that a significant amount of sialic acid was produced by VLP-containing fractions of the sucrose gradients and that these fractions corresponded to those fractions exhibiting hemagglutination activity.

Example 13

Figure 11:
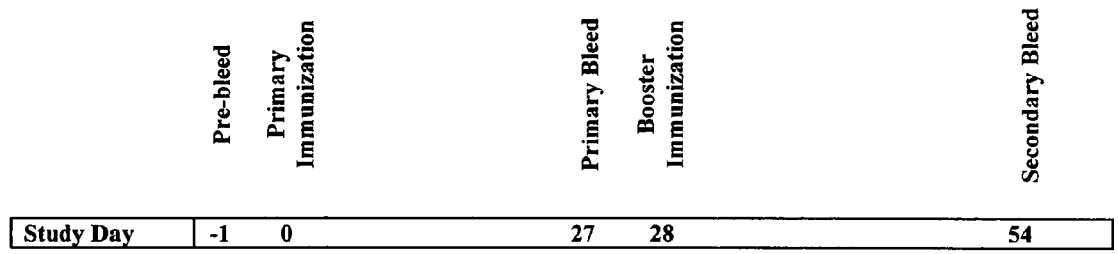

Immunization of BALB/c Mice with Functional Homotypic Recombinant Influenza H9N2 VLPs The immunogenicity of the recombinant influenza VLPs was ascertained by immunization of mice followed by Western blot analysis of immune sera. Recombinant VLPs (1 µg/injection) comprised of viral HA, NA, and M1 proteins from avian influenza virus type A/Honk Kong/1073/99 and purified on sucrose gradients were inoculated subcutaneously into the deltoid region of ten (10) female BALB/c mice at day 0 and day 28 (FIG. 11). PBS (pH 7.2) was administered similarly as a negative control into five (5) mice. The mice were bled from the supraorbital cavity at day-1 (pre-bleed), day 27 (primary bleed), and day 54 (secondary bleed). Sera were collected from blood samples following overnight clotting and centrifugation.

For Western blot analysis, 200 ng of inactivated avian influenza virus type A H9N2 or cold-adapted avian influenza virus type A H9N2, as well as See Blue Plus 2 pre-stained protein standards (InVitrogen), was denatured (95° C., 5 minutes) and subjected to electrophoresis under reduced conditions (10 mM β-mercaptoethanol) on 4-12% polyacrylamide gradient NuPAGE gels (InVitrogen) in MES buffer at 172 volts until the bromophenol blue tracking dye disappeared. For protein gels, the electrophoresed proteins were visualized by staining with Colloidal Coomassie Blue reagent (InVitrogen). Proteins were transferred from the gel to nitrocellulose membranes in methanol by the standard Western blot procedure. Sera from VLP-immunized mice and rabbits immunized with inactivated avian influenza virus H9N2 (positive control sera) were diluted 1:25 and 1:100, respectively, in PBS solution (pH 7.2) and used as primary antibody. Protein bound membranes, which were blocked with 5% casein, were reacted with primary antisera for 60 minutes at room temperature with constant shaking. Following washing of primary antibody membranes with phosphate buffered saline solution containing Tween 20, secondary antisera [goat anti-murine IgG—alkaline phosphatase conjugate (1:10,000) or goat anti-rabbit IgG—alkaline phosphatase conjugate (1:10,000)] were reacted 60 minutes with the membrane. Following washing of secondary antibody membranes with phosphate buffered saline solution containing Tween 20, antibody-binding proteins on the membranes were visualized by development with the chromogenic substrate such as NBT/BCIP (InVitrogen).

Figure 12:
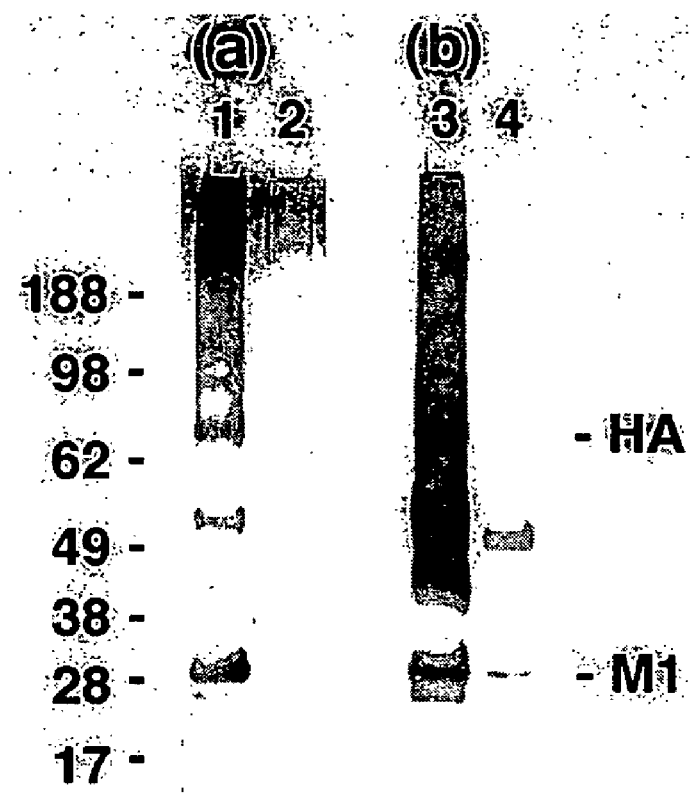

The results of Western blot analysis (FIG. 12) were that proteins with molecular weights similar to viral HA and M1 proteins (75 and 30 kd, respectively) bound to positive control sera (FIG. 12B) and sera from mice immunized with the recombinant influenza H9N2 VLPs (FIG. 12A). These results indicated that the recombinant influenza H9N2 VLPs alone were immunogenic in mice by this route of administration.

The following references are incorporated herein by reference:

Berglund, P., Fleeton, M. N., Smerdou, C., and Liljestrom, P. (1999). Immunization with recombinant Semliki Forest virus induces protection against influenza challenge in mice. *Vaccine* 17, 497-507.

Cox, J. C., and Coulter, A. R.(1997). Adjuvants—a classification and review of their modes of action. *Vaccine* 15, 248-256.

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. *Vaccine* 17, 2265-2274.

Crowther R A, Kiselev N A, Bottcher B, Berriman J A, Borisova G P, Ose V, Pumpens P. (1994). Three-dimensional structure of hepatitis B virus core particles determined by electron cryomicroscopy. Cell 17, 943-50.

Gomez-Puertas, P., Mena, I., Castillo, M., Vivo, A., Perez-Pastrana, E., and Portela, A. (1999). Efficient formation of influenza virus-like particles: dependence on the expression levels of viral proteins. *J. Gen. Virol.* 80, 1635-1645.

Johansson, B. E. (1999). Immunization with influenza A virus hemagglutinin and neuraminidase produced in recombinant baculovirus results in a balanced and broadened immune response superior to conventional vaccine. *Vaccine* 17, 2073-2080.

Lakey, D. L., Treanor, J. J., Betts, B. F., Smith, G. E., Thompson, J., Sannella, E., Reed, G., Wilkinson, B. E., and Wright, P. E. (1996) Recombinant baculovirus influenza A hemagglutinin vaccines are well tolerated and immunogenic in healthy adults. *J. Infect. Dis.* 174, 838-841.

Latham, T., and Galarza, J. M. (2001). Formation of wild-type and chimeric influenza virus-like particles following simultaneous expression of only four structural proteins. *J. Virol.* 75, 6154-6165.

Mena, I., Vivo, A., Perez, E., and Portela, A (1996). Rescue of a synthetic chloramphenicol acetyltransferase RNA into influenza-like particles obtained from recombinant plasmids. *J. Virol.* 70, 5016-5024.

Murphy, B. R., and Webster, R. G. (1996). Orthomyxoviruses. In "Virology" (D. M. K. B. N. Fields, P. M. Howley, Eds.) Vol. 1, pp. 1397-1445. Lippincott-Raven, Philadelphia.

Neumann, G., Watanabe, T., and Kawaoka, Y. (2000). Plasmid-driven formation of influenza virus-like particles. *J. Virol.* 74, 547-551.

Olsen, C. W., McGregor, M. W., Dybdahl-Sissoko, N., Schram, B. R., Nelson, K. M., Lunn, D. P., Macklin, M. D., and Swain, W. F. (1997). Immunogenicity and efficacy of baculovirus-expressed and DNA-based equine influenza virus hemagglutinin vaccines in mice. *Vaccine* 15, 1149-1156.

Peiris, J. S., Guan, Y., Markwell, D., Ghose, P., Webster, R. G., and Shortridge, K. F. (2001). Cocirculation of avian H9N2 and contemporary "human" H3N2 influenza A viruses in pigs in southwestern China: potential for genetic reassortment? *J. Virol.* 75, 9679-9686.

Pumpens, P., and Grens, E. (2003). Artificial genes for chimeric virus-like particles. In: "Artificial DNA" (Khudyakov, Y. E, and Fields, H. A., Eds.) pp. 249-327. CRC Press, New York.

Pushko, P., Parker, M., Ludwig, G. V., Davis, N. L., Johnston, R. E., and Smith, J. F. (1997). Replicon-helper systems from attenuated Venezuelan equine encephalitis virus: expression of heterologous genes in vitro and immunization against heterologous pathogens in vivo. *Virology* 239, 389-401.

Slepushkin, V. A., Katz, J. M., Black, R. A., Gamble, W. C., Rota, P. A., and Cox, N. J. (1995). Protection of mice against influenza A virus challenged by vaccination with baculovirus-expressed M2 protein. *Vaccine* 13, 1399-1402.

Treanor, J. J., Betts, R. F., Smith, G. E., Anderson, E. L., Hackett, C. S., Wilkinson, B. E., Belshe, R. B., and Powers, D. C. (1996). Evaluation of a recombinant hemagglutinin expressed in insect cells as an influenza vaccine in young and elderly adults. *J. Infect. Dis.* 173, 1467-1470.

Tsuji, M., et al. (1998). Recombinant Sindbis viruses expressing a cytotoxic T-lymphocyte epitope of a malaria parasite or of influenza virus elicit protection against the corresponding pathogen in mice. *J. Virol.* 72, 6907-6910.

Ulmer, J. B., et al. (1993). Heterologous protection against influenza by injection of DNA encoding a viral protein. *Science* 259, 1745-1749.

Ulmer, J. B., et al. (1998). Protective CD4+ and CD8+ T cells against influenza virus induced by vaccination with nucleoprotein DNA. *J. Virol.* 72, 5648-5653.

Watanabe, T., Watanabe, S., Neumann, G., and Kawaoka, Y. (2002) Immunogenicity and protective efficacy of replication-incompetent influenza virus-like particles. *J. Virol.* 76, 767-773.

Zhou, X., et al. (1995). Generation of cytotoxic and humoral immune responses by non-replicative recombinant Semliki Forest virus. *Proc. Natl. Acad. Sci. USA* 92, 3009-3013.

Other Embodiments

Those skilled in the art will recognize, or be able to ascertain using no more than routine experimentation, many equivalents to the specific embodiments of the invention described herein. Such equivalents are intended to be encompassed by the following claims:

TABLE 1

| Fraction#* | Titer |
| --- | --- |
| 1 | <1:500 |
| 3 | <1:500 |
| 5 | 1:500 |
| 7 | 1:1000 |
| 9 | 1:2000 |
| 11 | 1:2000 |
| 12 | 1:4000 |
| 14 | 1:500 |
| 16 | <1:500 |
| PBS** | <1:500 |
| A/Shangdong/9/93*** | 1:1000 |

*Fractions from 20-60% sucrose gradient
**Negative control
***Positive control

TABLE 2

| Virus | Strain | Gene | RT-PCR Primer | |
| --- | --- | --- | --- | --- |
| Type A (H3N2) | Sydney/5/97 | Hemagglutinin (HA) | Forward | 5'-A GGATCCATG AAGACTATCATTGCTTTGAG-3' (SEQ ID NO: 4) |
| | | | Reverse | 5'-A GGTACCTCAAATGCAAATGTTGCACCTAATG-3' (SEQ ID NO: 5) |
| | | Neuraminidase (NA) | Forward | 5'-GGGGACAAGTTTGTACAAAAAAGCAGGCTTAGAAG GAGATAGAACC ATG AATCCAAATCAAAAGATAATAAC-3' |

TABLE 2-continued

| Virus | Strain | Gene | RT-PCR Primer | |
|---|---|---|---|---|
| | | | Reverse | 5'-GGGGACCACTTTGTACAAGAAAGCTGGGTCCTATAT AGGCATGAGATTGATGTCCGC-3' (SEQ ID NO: 6) |
| | | Matrix (MI) | Forward | 5'-AAA GAATTC ATG AGTCTTCTAACCGAGGTCGAAACGTA-3' (SEQ ID NO: 7) |
| | | | Reverse | 5'-AAA TTCGAA TTACTCCAGCTCTATGCTGACAAAATGAC-3' (SEQ ID NO: 8) |
| | | M2 | Forward | 5'-A GAATTC ATG AGTCTTCTAACCGAGGTCGAAACGCCT ATCAGAAACGAATGGGGGTGC-3' (SEQ ID NO: 9) |
| | | | Reverse | 5'-AAA TTCGAA TTACTCCAGCTCTATGCTGACAAAATGAC-3' (SEQ ID NO: 10) |
| | | Nucleoprotein (NP) | Forward | 5'-A GAATTC ATG GCGTCCCAAGGCACCAACG-3' (SEQ ID NO: 11) |
| | | | Reverse | 5'-A GCGGCCGCTTAATTGTCGTACTCCTCTGCATTGTCTCCGAA GAAATAAG-3' (SEQ ID NO: 12) |
| Type B | Harbin | Hemagglutinin (HA) | Forward | 5'-A GAATTC ATG AAGGCAATAATTGTACTACTCATGG-3' (SEQ ID NO: 13) |
| | | | Reverse | 5'-A GCGGCCGCTTATAGACAGATGGGAGCAAGAAACATTGTC TCTGGAGA-3' (SEQ ID NO: 14) |
| | | Neuraminidase (NA) | Forward | 5'-A GAATT CATG CTACCTTCAACTATACAAACG-3' (SEQ ID NO: 15) |
| | | | Reverse | 5'-A GCGGCCGCTTACAGAGCCATATCAACACCTGTGACAGTG-3' (SEQ ID NO: 16) |

What is claimed:

1. A method of making an influenza virus-like particle (VLP), comprising expressing nucleic acids encoding influenza HA, NA, and M1 proteins in a cell culture expression system and purifying said VLPs from the cell culture supernatant, wherein said M1 protein is from an avian influenza virus; and wherein said M1 protein is from a different strain of influenza virus than said influenza HA protein and said influenza NA protein.

2. The method of claim 1, wherein said nucleic acids encoding HA, NA, and M1 proteins are expressed in a eukaryotic cell under conditions that permit the formation of VLPs.

3. The method of claim 2, wherein said eukaryotic cell is selected from the group consisting of yeast, insect, amphibian, avian and mammalian cells.

4. The method of claim 3, wherein said eukaryotic cell is an insect cell.

5. The method of claim 1, wherein said expression system is the baculovirus expression system.

6. The method of claim 1, wherein said HA and NA proteins are derived from an avian influenza virus.

7. The method of claim 6, wherein said HA and NA proteins are from an H9N2 avian influenza virus.

8. The method of claim 6, wherein said HA and NA proteins were isolated from an infected organism.

9. The method of claim 8, wherein said infected organism is human.

10. The method of claim 6, wherein said VLP exhibits hemagglutinin or neuraminidase activity.

11. The method of claim 6, wherein said VLP elicits neutralizing antibodies in a subject which are protective.

12. The method of claim 6, further comprising expressing nucleic acid from at least one M2 or NP protein.

13. The method of claim 6, wherein said VLP has a diameter of approximately 80 nm.

14. The method of claim 6, wherein said HA and NA proteins are from avian influenza A/Hong Kong/1073/99 (H9N2).

15. The method of claim 6, wherein said VLP exhibits hemagglutination activity at a titer of at least 1:500, when compared to a negative control.

16. The method of claim 6, wherein said VLP exhibits neuraminidase activity of at least an OD of 0.5 at a wavelength of 594 nm, when compared to a negative control, as determined chemically by measuring released sialic acid with thioarbitutic acid.

17. The method of claim 1, wherein said M1 protein is encoded by the nucleic acid of SEQ ID NO: 3.

18. The method of claim 6, wherein said M1 protein is encoded by the nucleic acid of SEQ ID NO: 3.

* * * * *

SEQUENCE LISTING

<160> NUMBER OF SEQ ID NOS: 17

<210> SEQ ID NO 1
<211> LENGTH: 1404
<212> TYPE: DNA
<213> ORGANISM: Avian influenza virus

<400> SEQUENCE: 1

```
atgaatccaa atcaaaagat aatagcactt ggctctgttt ctataactat tgcgacaata      60
tgtttactca tgcagattgc catcttagca acgactatga cactacattt caatgaatgt     120
accaacccat cgaacaatca agcagtgcca tgtgaaccaa tcataataga aaggaacata     180
acagagatag tgcatttgaa taatactacc atagagaagg aaagttgtcc taaagtagca     240
gaatacaaga attggtcaaa accgcaatgt caaattacag ggttcgcccc tttctccaag     300
gacaactcaa ttaggctttc tgcaggcggg gatatttggg tgacaagaga accttatgta     360
tcgtgcggtc ttggtaaatg ttaccaattt gcacttgggc agggaaccac tttgaacaac     420
aaacactcaa atggcacaat acatgatagg agtcccccata gaaccctttt aatgaacgag     480
ttgggtgttc catttcattt gggaaccaaa caagtgtgca tagcatggtc cagctcaagc     540
tgccatgatg gaaggcatg gttacatgtt tgtgtcactg gggatgatag aaatgcgact     600
gctagcatca tttatgatgg gatgcttacc gacagtattg gttcatggtc taagaacatc     660
ctcagaactc aggagtcaga atgcgtttgc atcaatggaa cttgtacagt agtaatgact     720
gatggaagtg catcaggaag ggctgatact aaaatactat tcattagaga agggaaaatt     780
gtccacattg gtccactgtc aggaagtgct cagcatgtgg aggaatgctc ctgttacccc     840
cggtatccag aagttagatg tgtttgcaga gacaattgga aagggctcca atagacccgtg     900 ctatatataa atgtggcaga ttatagtgtt gattctagtt atgtgtgctc aggacttgtt     960
ggcgacacac caagaaatga cgatagctcc agcagcagta actgcaggga tcctaataac    1020
```

```
gagagagggg gcccaggagt gaaagggtgg gcctttgaca atggaaatga tgtttggatg    1080
ggacgaacaa tcaagaaaga ttcgcgctct ggttatgaga ctttcagggt cgttggtggt    1140
tggactacgg ctaattccaa gtcacaaata aataggcaag tcatagttga cagtgataac    1200
tggtctgggt attctggtat attctctgtt gaaggaaaaa cctgcatcaa caggtgtttt    1260
tatgtggagt tgataagagg gagaccacag gagaccagag tatggtggac ttcaaatagc    1320
atcattgtat tttgtggaac ttcaggtacc tatggaacag gctcatggcc cgatggagcg    1380
aatatcaatt tcatgtctat ataa                                            1404
```

<210> SEQ ID NO 2
<211> LENGTH: 1683
<212> TYPE: DNA
<213> ORGANISM: Avian influenza virus

<400> SEQUENCE: 2

```
atggaaacaa tatcactaat aactatacta ctagtagtaa cagcaagcaa tgcagataaa     60
atctgcatcg gccaccagtc aacaaactcc acagaaactg tggacacgct aacagaaacc    120
aatgttcctg tgacacatgc caaagaattg ctccacacag agcataatgg aatgctgtgt    180
gcaacaagcc tgggacatcc cctcattcta gacacatgca ctattgaagg actagtctat    240
ggcaacccct cttgtgacct gctgttggga ggaagagaat ggtcctacat cgtcgaaaga    300
tcatcagctg taaatggaac gtgttaccct gggaatgtag aaaacctaga ggaactcagg    360 acactttttta gttccgctag ttcctaccaa agaatccaaa tcttcccaga cacaacctgg    420
aatgtgactt acactggaac aagcagagca tgttcaggtt cattctacag gagtatgaga    480
tggctgactc aaaagagcgg ttttttaccct gttcaagacg cccaatacac aaataacagg    540
ggaaagagca ttcttttcgt gtgggcata catcacccac ccacctatac cgagcaaaca    600
aatttgtaca taagaaacga cacaacaaca agcgtgacaa cagaagattt gaataggacc    660
ttcaaaccag tgatagggcc aaggcccctt gtcaatggtc tgcagggaag aattgattat    720
tattggtcgg tactaaaacc aggccaaaca ttgcgagtac gatccaatgg gaatctaatt    780
gctccatggt atggacacgt tcttttcagga gggagccatg gaagaatcct gaagactgat    840
ttaaaaggtg gtaattgtgt agtgcaatgt cagactgaaa aaggtggctt aaacagtaca    900
ttgccattcc acaatatcag taaatatgca tttggaacct gccccaaata tgtaagagtt    960
aatagtctca aactggcagt cggtctgagg aacgtgcctg ctagatcaag tagaggacta    1020
tttggagcca tagctggatt catagaagga ggttggccag gactagtcgc tggctggtat    1080
ggtttccagc attcaaatga tcaagggtt ggtatggctg cagatagggga ttcaactcaa    1140 aaggcaattg ataaaataac atccaaggtg aataatatag tcgacaagat gaacaagcaa    1200
tatgaaataa ttgatcatga attcagtgag gttgaaacta gactcaatat gatcaataat    1260
aagattgatg accaaataca agacgtatgg gcatataatg cagaattgct agtactactt    1320
gaaaatcaaa aaacactcga tgagcatgat gcgaacgtga acaatctata taacaaggtg    1380
aagagggcac tgggctccaa tgctatggaa gatgggaaag gctgtttcga gctataccat    1440
aaatgtgatg atcagtgcat ggaaacaatt cggaacggga cctataatag agaaagtat    1500 agagaggaat caagactaga aaggcagaaa atagaggggg ttaagctgga atctgaggga    1560
acttacaaaa tcctcaccat ttattcgact gtcgcctcat ctcttgtgct tgcaatgggg    1620
tttgctgcct tcctgttctg ggccatgtcc aatggatctt gcagatgcaa catttgtata    1680
```

-continued taa                                                                1683

<210> SEQ ID NO 3
<211> LENGTH: 759
<212> TYPE: DNA
<213> ORGANISM: Avian influenza virus

<400> SEQUENCE: 3
atgagtcttc taaccgaggt cgaaacgtac gttctctcta tcatcccatc aggccccctc      60
aaagccgaga tcgcgcagag acttgaggat gtttttgcag ggaagaacac agatcttgag     120
gctctcatgg aatggctaaa gacaagacca atcctgtcac ctctgactaa ggggatttta     180
gggtttgtgt tcacgctcac cgtgcccagt gagcgaggac tgcagcgtag acgatttgtc     240
caaaatgccc taaatgggaa tggagaccca acaacatgg acaggcagt taaactatac      300 aagaagctga gagggaaat gacattccat ggagcaaagg aagttgcact cagttactca     360
actggtgcgc ttgccagttg catgggtctc atatacaacc ggatgggaac agtgaccaca     420
gaagtggctc ttggcctagt atgtgccact tgtgaacaga ttgctgatgc ccaacatcgg     480
tcccacaggc agatggcgac taccaccaac ccactaatca ggcatgagaa cagaatggta     540
ctagccagca ctacggctaa ggccatggag cagatggctg atcaagtga gcaggcagca     600 gaagccatgg aagtcgcaag tcaggctagg caaatggtgc aggctatgag gacaattggg     660
actcacccta gttccagtgc aggtctaaaa gatgatctta ttgaaaattt gcaggcttac     720
cagaaacgga tgggagtgca aatgcagaga ttcaagtga                           759

<210> SEQ ID NO 4
<211> LENGTH: 30
<212> TYPE: DNA
<213> ORGANISM: Artificial Sequence
<220> FEATURE:
<223> OTHER INFORMATION: Hemagglutinin (HA) Sydney/5/97 Forward Primer

<400> SEQUENCE: 4
aggatccatg aagactatca ttgctttgag                                      30

<210> SEQ ID NO 5
<211> LENGTH: 32
<212> TYPE: DNA
<213> ORGANISM: Artificial Sequence
<220> FEATURE:
<223> OTHER INFORMATION: Hemagglutinin (HA) Sydney/5/97 Reverse Primer

<400> SEQUENCE: 5
aggtacctca aatgcaaatg ttgcacctaa tg                                   32

<210> SEQ ID NO 6
<211> LENGTH: 72
<212> TYPE: DNA
<213> ORGANISM: Artificial Sequence
<220> FEATURE:
<223> OTHER INFORMATION: Neuraminidase (NA) Sydney/5/97 Forward Primer

<400> SEQUENCE: 6 gggacaagt ttgtacaaaa aagcaggctt agaaggagat agaaccatga atccaaatca      60
aaagataata ac                                                         72

<210> SEQ ID NO 7
<211> LENGTH: 57
<212> TYPE: DNA
<213> ORGANISM: Artificial Sequence

```
<220> FEATURE:
<223> OTHER INFORMATION: Neuraminidase (NA) Sydney/5/97 Reverse Primer

<400> SEQUENCE: 7
ggggaccact tgtacaaga aagctgggtc ctatataggc atgagattga tgtccgc         57

<210> SEQ ID NO 8
<211> LENGTH: 38
<212> TYPE: DNA
<213> ORGANISM: Artificial Sequence
<220> FEATURE:
<223> OTHER INFORMATION: Matrix (M1) Sydney/5/97 Forward Primer

<400> SEQUENCE: 8
aaagaattca tgagtcttct aaccgaggtc gaaacgta                             38

<210> SEQ ID NO 9
<211> LENGTH: 38
<212> TYPE: DNA
<213> ORGANISM: Artificial Sequence
<220> FEATURE:
<223> OTHER INFORMATION: Matrix (M1) Sydney/5/97 Reverse Primer

<400> SEQUENCE: 9
aaattcgaat tactccagct ctatgctgac aaaatgac                             38

<210> SEQ ID NO 10
<211> LENGTH: 58
<212> TYPE: DNA
<213> ORGANISM: Artificial Sequence
<220> FEATURE:
<223> OTHER INFORMATION: M2 Sydney/5/97 Forward Primer

<400> SEQUENCE: 10
agaattcatg agtcttctaa ccgaggtcga acgccatc agaaacgaat gggggtgc         58

<210> SEQ ID NO 11
<211> LENGTH: 38
<212> TYPE: DNA
<213> ORGANISM: Artificial Sequence
<220> FEATURE:
<223> OTHER INFORMATION: M2 Sydney/5/97 Reverse Primer

<400> SEQUENCE: 11
aaattcgaat tactccagct ctatgctgac aaaatgac                             38

<210> SEQ ID NO 12
<211> LENGTH: 29
<212> TYPE: DNA
<213> ORGANISM: Artificial Sequence
<220> FEATURE:
<223> OTHER INFORMATION: Nucleoprotein (NP) Sydney/5/97 Forward Primer

<400> SEQUENCE: 12
agaattcatg gcgtcccaag gcaccaacg                                       29

<210> SEQ ID NO 13
<211> LENGTH: 50
<212> TYPE: DNA
<213> ORGANISM: Artificial Sequence
<220> FEATURE:
<223> OTHER INFORMATION: Nucleoprotein (NP) Sydney/5/97 Reverse Primer

<400> SEQUENCE: 13
agcggccgct taattgtcgt actcctctgc attgtctccg aagaaataag                50
```

```
-continued

<210> SEQ ID NO 14
<211> LENGTH: 35
<212> TYPE: DNA
<213> ORGANISM: Artificial Sequence
<220> FEATURE:
<223> OTHER INFORMATION: Type B Harbin Hemagglutinin (HA) Forward Primer

<400> SEQUENCE: 14
agaattcatg aaggcaataa ttgtactact catgg                                 35

<210> SEQ ID NO 15
<211> LENGTH: 47
<212> TYPE: DNA
<213> ORGANISM: Artificial Sequence
<220> FEATURE:
<223> OTHER INFORMATION: Type B Harbin Hemagglutinin (HA) Reverse Primer

<400> SEQUENCE: 15
agcggccgct tatagacaga tggagcaaga aacattgtct ctggaga                    47

<210> SEQ ID NO 16
<211> LENGTH: 31
<212> TYPE: DNA
<213> ORGANISM: Artificial Sequence
<220> FEATURE:
<223> OTHER INFORMATION: Type B Harbin Neuraminidase (NA) Forward Primer

<400> SEQUENCE: 16
agaattcatg ctaccttcaa ctatacaaac g                                     31

<210> SEQ ID NO 17
<211> LENGTH: 40
<212> TYPE: DNA
<213> ORGANISM: Artificial Sequence
<220> FEATURE:
<223> OTHER INFORMATION: Type B Harbin Neuraminidase (NA) Reverse Primer

<400> SEQUENCE: 17
agcggccgct tacagagcca tatcaacacc tgtgacagtg                            40
```